(12) United States Patent
Co et al.

(10) Patent No.: US 11,340,225 B2
(45) Date of Patent: May 24, 2022

(54) ANTIBODY-DEPENDENT CELL-MEDIATED PHAGOCYTOSIS ASSAY FOR RELIABLY MEASURING UPTAKE OF AGGREGATED PROTEINS

(71) Applicant: Biogen International Neuroscience GmbH, Baar (CH)

(72) Inventors: Carl Co, Somerville, MA (US);
Allyson Masci, Somerville, MA (US);
Svetlana Bergelson, Newton, MA (US)

(73) Assignee: Biogen International Neuroscience GmbH, Baar (CH)

( * ) Notice: Subject to any disclaimer, the term of this patent is extended or adjusted under 35 U.S.C. 154(b) by 275 days.

(21) Appl. No.: 16/083,695

(22) PCT Filed: Mar. 14, 2017

(86) PCT No.: PCT/EP2017/056031
§ 371 (c)(1),
(2) Date: Sep. 10, 2018

(87) PCT Pub. No.: WO2017/157961
PCT Pub. Date: Sep. 21, 2017

(65) Prior Publication Data
US 2019/0079077 A1    Mar. 14, 2019

Related U.S. Application Data

(60) Provisional application No. 62/308,082, filed on Mar. 14, 2016.

(51) Int. Cl.
*G01N 33/569* (2006.01)
*G01N 33/50* (2006.01)

(52) U.S. Cl.
CPC ... *G01N 33/56972* (2013.01); *G01N 33/5008* (2013.01); *G01N 33/5032* (2013.01);
(Continued)

(58) Field of Classification Search
CPC .......... G01N 33/5055; G01N 33/5008; G01N 33/5032; G01N 33/56966; G01N 33/56972
See application file for complete search history.

(56) References Cited

U.S. PATENT DOCUMENTS

2003/0028904 A1    2/2003  Gumienny et al.
2009/0104629 A1    4/2009  Fiala
(Continued)

FOREIGN PATENT DOCUMENTS

WO    WO 2008081008      7/2008
WO    WO-2010/069603 A1  6/2010
(Continued)

OTHER PUBLICATIONS

Knowles et al. The p75 Neurotrophin Receptor Promotes Amyloid-ß(1-42)-Induced Neuritic Dystrophy In Vitro and In Vivo. The Journal of NeuroScience 29 (34): 10627-10637 (Aug. 26, 2009).*
(Continued)

*Primary Examiner* — Gailene Gabel
(74) *Attorney, Agent, or Firm* — Choate, Hall & Stewart LLP; Stephanie L. Schonewald; Tracy L. Vrablik

(57) ABSTRACT

The present disclosure provides methods of assaying for antibody-dependent cell-mediated phagocytosis (ADCP). In some embodiments, the methods include monomerizing and labeling a protein, contacting the protein with a protein-specific antibody to form an antibody-protein complex, contacting the antibody-protein complex with a phagocytic cell to permit phagocytosis, and assessing the amount of internalized fluorescence.

47 Claims, 13 Drawing Sheets

(52) U.S. Cl.
CPC ..... *G01N 33/5055* (2013.01); *G01N 33/5094* (2013.01); *G01N 33/56966* (2013.01)

(56) References Cited

U.S. PATENT DOCUMENTS

| | | | | |
|---|---|---|---|---|
| 2010/0202968 A1* | 8/2010 | Nitsch | ............... | A61P 9/00 424/9.1 |
| 2019/0338048 A1* | 11/2019 | Urosev | ............ | C07K 16/46 |

FOREIGN PATENT DOCUMENTS

| WO | WO-2012/049570 A1 | 4/2012 |
|---|---|---|
| WO | WO-2012/177972 A1 | 12/2012 |
| WO | WO 2013020723 | 2/2013 |
| WO | WO-2013/061163 A2 | 5/2013 |
| WO | WO-2014/100600 A2 | 6/2014 |
| WO | WO-2017/157961 A1 | 9/2017 |

OTHER PUBLICATIONS

Webster et al. Antibody-Mediated Phagocytosis of the Amyloid ß-Peptide in Microglia Is Differentially Modulated by C1q. The Journal of Immunology 166: 7496-7503 (2001).*
International Preliminary Report on Patentability in International Application No. PCT/EP2017/056031, dated Sep. 18, 2018, 8 pages.
International Search Report and Written Opinion in International Application No. PCT/EP2017/056031, dated May 10, 2017, 11 pages.
Knowles, et al., ""The p75 Neurotrophin Receptor Promotes Amyloid-ß (1-42)-Induced Neuritic Dystrophy In Vitro and In Vivo"", Journal of Neuroscience, 2009, 29(34):10627-10637.
Van Muiswinkel et al., "The amino-terminus of the amyloid-ß protein is critical for the cellular binding and consequent activation of the respiratory burst of human macrophages," Journal of Neuroimmunology, 1999, 96(1):121-130.
Webster et al., "Antibody-mediated phagocytosis of the amyloid ß-peptide in microglia is differentially modulated by C1q," The Journal of Immunology, 2001, 166(12):7496-7503.
Ackerman et al., 2013. Enhanced phagocytic activity of HIV-specific antibodies correlates with natural production of immunoglobulins with skewed affinity for FcγR2a and FcγR2b. J. Viral. 87, 5468.
Adolfsson et al. (2012) J Neurosci. Jul. 11, 2012;32(28):9677-89.
Berkovich, et al., Distinct modulation of microglial amyloid bphagocytosis and migration by neuropeptidesi, Journal of Neuroinflammation, 7:61 (2010).
Bohrmann et al., 2012. Journal of Alzheimer's Disease 28, 49-69. Gantenerumab: A Novel Human Anti-Aß Antibody Demonstrates Sustained Cerebral Amyloid-13 Binding and Elicits Cell-Mediated Removal of Human Amyloid-13.
Bouter et al., Abeta targets of the biosimilar antibodies of Bapineuzumab, Crenezumab, Solanezumab in comparison to an antibody against N-truncated Abeta in sporadic Alzheimer disease cases and mouse models, Acta Neuropathologica vol. 130, pp. 713-729 (2015).
Burstein et al., 2013. Safety and pharmacology of ponezumab (PF-04360365) after a single 10-minute intravenous infusion in subjects with mild to moderate Alzheimer disease. Clin Neuropharmacol. Jan.-Feb. 2013;36(1):8-13. PMID: 23334069.
Ferreira et al., 2011. Neuropeptide Y inhibits interleukin-lb-induced phagoeytosis by microglial cells, J Neuroinflammation 8:169.
Gallo et al., 2010. The influence of IgG density and macrophage Fc (gamma) receptor cross-linking on phagoeytosis and IL-10 production. Immunol. Lett. 133, 70.
Glabe et al., 2004. Conformation-dependent antibodies target diseases of protein misfolding, Trends in Biochemical Sciences, 29(10) 542-547.
Golde, T. E. et al., Thinking laterally about neurodegenerative proteinopathies, J Clinic Inv., 123(5):1847-1855 (2013).
Horton et al., 2010. Fc-engineered anti-CD40 antibody enhances multiple effector functions and exhibits potent in vitro and in vivo antitumor activity against hematological malignancies. Blood, 116, 3004.
Lannfelt et al.. Perspectives on future Alzheimer therapies: amyloid-? protofibrils—a new target for immunotherapy with BAN2401 in Alzheimer's disease 2014 Alzheimers Res Ther. 2014; 6(2): 16.
Indik et al., 1995. The molecular dissection of Fc gamma receptor mediated phagocytosis. Blood 86: 4389-4399.
Lundholt et al., 2003. A simple technique for reducing edge effect in cell-based assays. J Biomolecular Screening 566-570.
Oflazoglu et al., 2009. Macrophages and Fc-receptor interactions contribute to the antitumor activities of the anti-CD40 antibody SGN-40. Br. J. Cancer, 100, 113.
Panda, S. K. and Ravindan, B., In Vitro Culture of Human PBMCs, Bio-Protocol, 3(3):1-3 (2013).
Parekh et al., 2012. Development and validation of an antibody-dependent cell-mediated cytotoxicity-reporter gene assay. mAbs 4:3, 310-318.
Park et al., 2012. Genetic Polymorphisms of FcgRIIa and FcgRIIIa are not predictive of clinical outcomes after cetuximab plus irinotecan chemotherapy in patients with colorectal cancer. Oncology 82(2): 83-9.
Patel. Biogen's aducanumab raises hope that Alzheimer's can be treated at its source. Manag Care. Jun. 2015;24(6):19. PubMed PMID: 26182718.
Richards et al. Optimization of antibody binding to FcgammaRIIa enhances macrophage phagocytosis of tumor cells. Mol. Cancer. Ther. 7, 2517.
Schlee et al., 2006. Quantitative analysis of the activation mechanism of the multicomponent growth-factor receptor Ret. Nature Chemical Biology 11: 636-644.
Selvaraj et al., 1988. The major Fc receptor in blood has a phosphatidylinositol anchor and is deficient in paroxysmal nocturnal haemoglobinuria. Nature 333.
Shashidharamurthy et al., 2009. Dynamics of the interactions of Human IgG subtype immune complexes with cells expressing R and H allelic forms of a low-affinity Fcγ Receptor CD32A. J Immunol 183: 8216-8224.
Ulvestad et al., 1994. Fc receptors for IgG on cultured human microglia mediate cytotoxicity and phagocytosis of antibody-coated targets. J Neuropathol Exp Neuro, 53 (1): 27-36.
Vieth et al., 2010. Differential requirement of lipid rafts for FcgRIIA mediated effector activities. Cell Immunol. 265(2): 111-110.
Webster et al., 2001. Antibody-Mediated Phagocytosis of the Amyloid b-peptide in microglia is differentially modulated by C1q. J Immunol 166: 7496-7503.
Yanamandra, K. et al., Anti-tau antibody reduces insoluble tau and decreases brain atrophy, ANNALS, 2(3):278-288 (2015).
Zhang et al., 2010. Coordination of Fc receptor signaling regulates cellular commitment to phagocytosis. Proc. Natl. Acad. Sci. U SA. 107, 19332.

* cited by examiner

NO ADUCANUMAB

+ADUCANUMAB

ANTIBODY-DEPENDENT CELL-MEDIATED PHAGOCYTOSIS ASSAY FOR RELIABLY MEASURING UPTAKE OF AGGREGATED PROTEINS

CROSS REFERENCE TO RELATED APPLICATIONS

This application is the National Stage of International Application No. PCT/EP2017/056031, filed on Mar. 14, 2017, which claims priority to U.S. Provisional Appl. No. 62/308,082 filed Mar. 14, 2016 The disclosure of the prior applications is incorporated herein by reference in their entirety.

BACKGROUND

Phagocytosis is a process by which an extracellular molecule or a molecule bound to the surface of the cell is engulfed by a phagocytic cell. Antibody-dependent cell-mediated phagocytosis (ADCP) is a complex mechanism by which antibodies bind to their targets, recruit phagocytic cells, and cause engulfment of their target into phagosomes (see, FIG. 1). Confirming the ability of an antibody to mediate ADCP is currently done using techniques such as flow cytometry and confocal microscopy. Many of the assays used require complex instrumentation, are not high-throughput, and/or require complex data analyses. In addition, when measuring ADCP of antibodies that bind to aggregated proteins, the prior art assays do not yield consistent results. Thus, there is significant unmet need for consistent, robust and high-throughput methods to measure ADCP of aggregated proteins, e.g., for product characterization and/or stability testing.

SUMMARY OF THE INVENTION

This disclosure relates to methods for assaying antibody-dependent cell-mediated phagocytosis. In a certain aspect, the disclosure relates to a highly robust assay for measuring antibody-dependent cell-mediated phagocytosis by labeling a protein, contacting the protein with a protein-specific antibody to form an antibody-protein complex, contacting the antibody-protein complex with a phagocytic cell to permit phagocytosis, and assessing the amount of internalized label. In particular, the invention pertains to novel assays for measuring uptake of aggregated proteins. ADCP assays and methods for measuring intracellular phagocytosis events for antibodies that bind to aggregated proteins are provided herein. The assays may be implemented in a high-throughput configuration and/or with high accuracy and precision in a laboratory, e.g., to evaluate the properties of one or more antibodies.

In some embodiments, assaying ADCP comprises the steps of monomerizing and fluorescently labeling an aggregated protein, contacting the protein with a protein-specific antibody to form an antibody-protein complex, contacting the antibody-protein complex with a phagocytic cell to permit phagocytosis, and measuring intracellular fluorescence. In some embodiments, the phagocytic cell engulfs the antibody-protein complex. The internalized fluorescence may be visualized and assessed by microscopy, e.g., transmission electron microscopy. Alternatively, the internalized fluorescence may be measured using flow cytometry, e.g., fluorescence-activated cell sorting (FACS). In some embodiments, fluorescence measured from the assay is specific to phagocytosed proteins. Advantageously, the FACS-based assay provides consistent, accurate, and precise measurements of internalized fluorescence and phagocytic events, and also allows for higher throughput analysis relative to current ADCP assays.

DETAILED DESCRIPTION

Definitions

Figure 1:
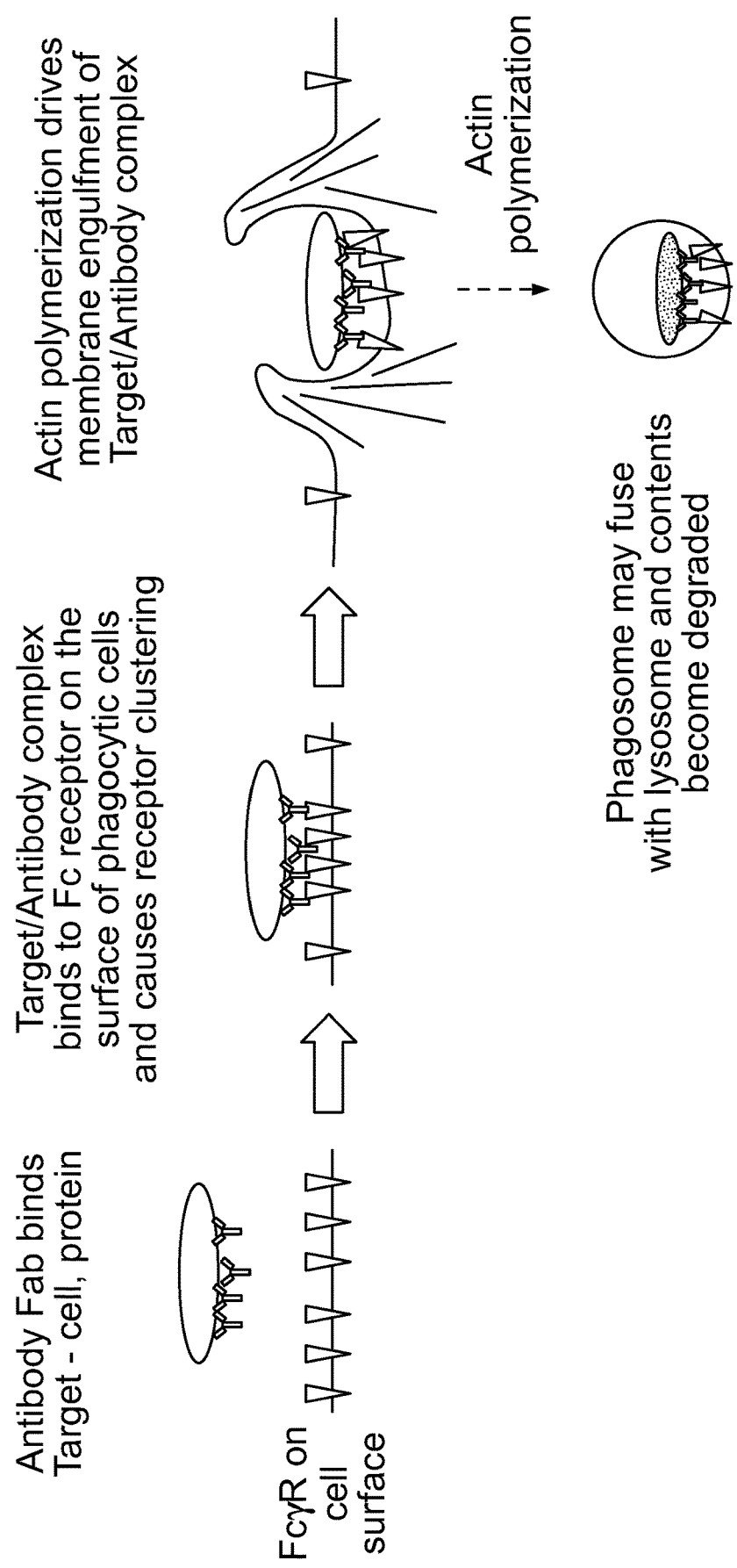
FIG. 1 depicts an exemplary schematic for an antibody-dependent cell-mediated phagocytosis (ADCP) process. In the first step of ADCP, the Fab region of antibodies binds to the target proteins. Next, the target/antibody complex binds and clusters the Fc gamma receptor (FcγR) on the surface of phagocytic cells. The clustering of FcγRs results in phagocytosis of the target/antibody complex. Actin polymerization is required for phagocytosis. The phagosome may fuse with lysosome resulting in degradation of the target protein.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

"Antibody-dependent cell-mediated phagocytosis" and "ADCP" are used interchangeably to refer to the mechanism(s) by which Fc receptors of phagocytic cells bind to antibodies that are attached to aggregated proteins (e.g., dimeric, protofibrillar, and/or fibrillar forms of a protein) and stimulate the phagocytic cells to internalize the protein. In some aspects, methods of assaying for ADCP comprise fluorescently labeling a protein, e.g., Aβ; contacting the aggregated protein with an antibody that binds to the aggregated protein, to form an antibody-protein complex; contacting the antibody-protein complex with a phagocytic cell to permit phagocytosis; in one embodiment, if the phagocytic cell is an adherent cell, the cell is removed with non-enzymatic cell dissociation buffer, and contacted with the antibody-protein complex.

Once the antibody protein complex has been contacted with cells and phagocytosis is allowed to occur, the amount of internalized aggregated protein is assessed by measuring internalized fluorescence, e.g., by flow cytometry. As described herein, an ADCP assay can be used to evaluate the protein-binding properties and/or the Fc effector functions of an antibody.

As used herein, an "antibody" is a glycoprotein comprising at least two heavy (H) chains and two light (L) chains inter-connected by disulfide bonds. Each heavy chain comprises a heavy chain variable region (VH) and a heavy chain constant region. The heavy chain constant region comprises three domains, CH1, CH2, and CH3. Each light chain comprises a light chain variable region (VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with a protein. The constant regions of the antibodies may mediate the binding of the immunoglobulin to host tissues or factors, including various cells of the immune system (e.g., effector cells) and the first component (C1q) of the classical complement system.

Antibodies may be a monoclonal antibodies or polyclonal antibodies. A "monoclonal antibody" refers to a preparation of antibody molecules of single molecular composition and/or obtained from a population of substantially homogenous antibodies. A monoclonal antibody displays a single binding specificity and affinity for a particular epitope. A "polyclonal antibody" refers to a heterogeneous pool of antibodies produced by a number of different B lymphocytes. Different antibodies in the pool recognize and specifically bind different epitopes. An "epitope" refers to a polypeptide sequence that, by itself or as part of a larger sequence, binds to an antibody generated in response to the sequence. A target protein, e.g., Aβ, may contain linear, discontinuous epitopes, and/or conformational epitopes.

In some embodiments, the antibodies are humanized antibodies. A "humanized antibody" refers to an antibody that retains only the protein-binding CDRs from the parent antibody in association with human framework regions (see, Waldmann, 1991, Science 252:1657). In some embodiments, the antibodies are human antibodies. A "human antibody" refers to antibodies having variable and constant regions derived from human germline immunoglobulin sequences or from a human subject. Human antibodies can include amino acid residues not encoded by human germline immunoglobulin sequences (e.g., mutations introduced by random or site-specific mutagenesis in vitro or by somatic mutation in vivo). The term "human antibody," as used herein, does not include antibodies in which CDR sequences derived from the germline of another mammalian species, such as a mouse have been grafted onto human framework sequences (referred to herein as "humanized antibodies"). In some embodiments, the antibodies are chimeric antibodies. A "chimeric antibody" refers to an antibody that combines the murine variable or hypervariable regions with the human constant region or constant and variable framework regions. In some embodiments, the antibodies are bispecific or multispecific antibodies.

In some embodiments, the antibodies are recombinant antibodies. A "recombinant antibody" refers to antibodies that are prepared, expressed, created, or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

As used herein, "aggregated protein" refers to a protein that forms a structure comprising more than one monomer, e.g., a dimer, oligomer, protofibril, or fibril. Fibrillization of proteins refers to the process by which a protein monomer forms a polymeric fibril or aggregate, e.g., by first forming dimers, oligomers, and/or protofibrils. Peptide or protein fibrillization is relevant to many diseases based on the deposition of amyloids, e.g., diseases characterized by amyloidosis. Exemplary proteins that form aggregates and can be used in the assays of the instant invention include amyloid beta (A$\beta$), tau, alpha-synuclein, TDP-43, neuroserpin, FUS, prion proteins (PrP$^{SC}$), SOD1, ubiquilin, optineurin, ABri, and ADan (see, e.g., Golde et al., 2013).

As used herein, "monomerize" refers to a process by which aggregated proteins, e.g., dimers, oligomers, protofibrils, and/or fibrils, are separated or converted into their monomeric state. In some embodiments, a substantial population of the aggregated proteins are separated or converted into monomers. In some embodiments, all of the aggregated proteins are separated or converted into monomers. In some embodiments, the aggregated protein is treated with an agent, e.g., hydroxyfluoroisopropanol, to separate or convert the aggregated proteins into monomers. Other suitable agents are known in the art.

A "detectable label" refers to a chemical or radiochemical molecule that can be directly or indirectly detected and quantified by methods known in the art. In some embodiments, a detectable label is a tag, a protein modification, a dye, radioactive dye, an enzyme, a fluorophore, a chromophore, a metal colloid, a chemiluminescent molecule, or a bioluminescent molecule. Examples of commonly used detectable labels include, but are not limited to, histidine tag, GST tag, FLAG tag, MBP tag, sulfoindocyanine Cy dyes, 3H, 32P, 35S, 125I, 14C, europium, horseradish peroxidase, penicillinase, alkaline phosphatase, FITC, HiLyte, FAM, rhodamine, fluorescein, Lucifer yellow, green fluorescent protein, red fluorescent protein, and Alexa fluorophores.

"Labeling" a molecule refers to the formation of linkage (e.g., covalent linkages) between two molecules. An antibody, protein, or antibody-protein complex may be labeled with a first molecule that may be a protein, a peptide, a vitamin, a nucleic acid, and/or another chemical composition. In some embodiments, a protein is directly or indirectly labeled with a detectable label. In alternate embodiments, an antibody that facilitates Fc-mediated phagocytosis of the protein is directly or indirectly labeled with a detectable label. In some embodiments, both the antibody and the protein are labeled. In some embodiments, a protein, e.g., A$\beta$, is labeled with a first molecule that is a detectable label. In some embodiments, a protein is labeled with a fluorescent label, e.g., HiLyte488-A$\beta$. Some embodiments require contacting the first molecule with a second molecule to facilitate detection. In some embodiments, the first and second molecules may be biotin and streptavidin, biotin and neutravidin, biotin and capavidin, fluorescein and an anti-fluorescein antibody, polyhistine and nickel or cobalt chelate complex, glutathione S-transferase and glutathione, calmodulin and calmodulin-binding peptide, a lectin and carbohydrate binding ligand, or another suitable binding pair. In some embodiments, the first and second molecules interact in a non-covalent manner. The interaction between the first and second molecules may be stable or transient. The interaction between the first and second molecules may be reversible or irreversible.

"Antibody-protein complex" refers to a complex of an antibody and the protein to which it specifically binds. For example, in some embodiments, the antibody-protein protein complex comprises an anti-$\beta$-amyloid antibody bound to A$\beta$. In some embodiments, the antibody-protein complex comprises an Aducanumab antibody bound to A$\beta$.

As used herein, an antibody that is "specific" for a protein refers to an antibody that binds to a protein via its complementarity determining regions and does not include non-specific binding. For example, the anti-$\beta$-amyloid antibody, Aducanumab, binds specifically to $\beta$-amyloid. Typically, the antibody binds with an affinity that is at least two-fold greater than its affinity for binding to an unrelated protein (e.g., BSA, casein) protein. Antibodies provided herein encompass various antibody isotypes, such as IgG1, IgG2, IgG3, IgG4, IgM, IgA1, IgA2, IgAsec, IgD, IgE. In one embodiment, antibodies for use in connection with the assays of the invention bind to aggregated forms of a protein (e.g., whether soluble or insoluble), and do not bind to monomeric forms of the same protein.

As used herein, "isotype" refers to the antibody class (e.g., IgM or IgG1) that is encoded by heavy chain constant region genes.

Antibody-dependent cell-mediated assays provided herein may be used to measure activity of any suitable antibodies including, but not limited to, Aducanumab (Patel 2015; WO 2008/081008), Bapineuzumab (Bouter et al., 2015), Gantenerumab (Bohrmann et al., 2012), Crenezumab (Bouter et al., 2015), BAN2401 (Lannfelt et al., 2014; PCT/SE2007/000292), Ponezumab (Burstein et al., 2013), Solanezumab (Bouter et al., 2015), anti-tau antibodies (Yanamandra et al., 2015; WO 2012/049570; WO 2014/100600), anti-synuclein antibodies (WO 2012/177972; WO 2010/069603), anti-TDP-43 antibodies (WO 2013/061163). In some embodiments, the antibody binds strongly to aggregated proteins (e.g., dimeric, protofibrillar, and/or fibrillar forms of a protein) and weakly to monomeric proteins (e.g., in the case of Ab: Aducanumab, Gantenerumab, BAN2401). In some embodiments, the antibody binds to monomeric proteins (e.g., in the case of Ab: Bapineuzumab, Crenezumab). Other exemplary antibodies that bind to aggregated proteins, e.g., tau, alpha-synuclein, TDP-43, neuroserpin, FUS, prion proteins (PrP$^{SC}$), SOD1, ubiquilin, optineurin, ABri, and Adan are known in the art or could be identified using standard techniques. Antibodies are also known in the art that bind to conformation-dependent epitopes on aggregated proteins and such antibodies can also be used in the subject assays (e.g., Glabe. 2004. TRENDS in Biochemical Sciences 29: volume 10). The instant assays enable rapid and accurate testing of such antibodies to confirm their ability to mediate phagocytosis of these aggregated proteins by cells.

Antibody-dependent cell-mediated assays of the present disclosure include phagocytic cells. The process of phagocytosis refers to the uptake or engulfment of an extracellular molecule or a molecule bound to the surface of the cell. Many different cells and cell types are capable of performing phagocytosis and appropriate cells for use in ADCP assay provided herein will be evident to one skilled in the art. In some embodiments, cells used for ADCP assays are mammalian cells, insect cells, fungal cells, or yeast cells. In some embodiments, the mammalian cells are isolated from a human, a mouse, a rat, a hamster, an ape, a monkey or a dog. In some embodiments, the cells are professional phagocytic cells, including, but not limited to, neutrophils, monocytes, macrophages, dendritic cells, and/or mast cells. In other embodiments, the cells are non-professional phagocytes including, but not limited to, epithelial cells, endothelial cells, fibroblasts, and/or mesenchymal cells. Other phagocytic cells may be used in accordance with the disclosure.

In some embodiments, the phagocytic cells are primary cells. In other embodiments, the phagocytic cells are immortalized cells. In some embodiments, the phagocytic cells belong to an established cell line. Examples of commonly used cell lines include, without limitation, BV-2, THP-1, CHO, 293-T, 3T3, 4T1, 721, 9L, A2780, A172, A20, A253, A431, A-549, ALC, B16, B35, BCP-1, BEAS-2B, bEnd.3, BHK-21, BR293, BxPC3, C3H-10T1/2, C6, Cal-27, COR-L23, COS-7, CML T1, CMT, CT26, D17, DH82, DU145, DuCaP, EL4, EM2, EM3, EMT6/AR1, FM3, H1299, H69, HB54, HB55, HCA2, HEK-293, HeLa, Hepa1c1c7, HL-60, HMEC, HT-29, HUVEC, Jurkat, J558L, JY, K562, Ku812, KCL22, KG1, KY01, MCF-7, RBL, Saos-2, SKBR3, SKOV-3, T2, T-47D, T84, U373, U937, Vero, and J774.

In some embodiments, the cell lines are naturally phagocytic cell lines. In alternate embodiments, the cell lines are non-naturally phagocytic cell lines that are engineered to express a heterologous sequence that confers phagocytic capability, e.g., a sequence that encodes a human Fc receptor. Phagocytic cells may be adherent phagocytic cells, meaning that the cells, when cultured on a surface (e.g., cell culture dish), attach to the surface, e.g., in a monolayer. Alternatively, phagocytic cells may be non-adherent cells grow in suspension without attaching to a surface.

A "heterologous" nucleic acid sequence refers to a nucleic acid sequence not naturally associated with a host genome into which it is introduced, e.g., a CHO cell that stably or transiently expresses human FcγR2A/CD32A. In some embodiments, a "heterologous" nucleic acid sequence refers to a non-naturally occurring multiple copies of a naturally occurring nucleic acid sequence.

"Fc-mediated phagocytosis" refers to the uptake of extracellular or surface-bound molecule(s) mediated by the interaction between a Fc-receptor (FcR) on the surface of the phagocytic cell and the Fc portion of an antibody. In some embodiments, the FcR is an FcγR, FcαR, or FcεR family member. In some embodiments, the phagocytic cell endogenously expresses the FcR. In other embodiments, the cell has been modified to express the FcR. In some embodiments, the expression of FcRs on non-phagocytic cells such as Chinese Hamster Ovary (CHO) cells or COS-1 cells is sufficient to endow these FcR-CHO cells with phagocytic activity (Vieth et al. 2010; Indik et al., 1995). In some embodiments, CHO-Fc gamma R2a cells (CHO-CD32A) cells are capable of performing Fc-dependent uptake of IgG-bound proteins (Indik et al., 1995).

"Amyloid β" and "Aβ" are used interchangeably to refer to amyloid β peptide and modifications, fragments, and/or equivalents thereof. In particular, "amyloid β" and "Aβ" as used herein refers to any fragment produced by the proteolytic cleavage of amyloid precursor protein (APP).

As used herein, "flow cytometry" refers to a technique in which cells are suspended in a stream of fluid and passed through an electronic detection device. "Fluorescence-activated cell sorting" or "FACS" refers to a type of flow cytometry in which cells are fluorescently labeled, passed through an electronic detection device single file, excited by a laser, and measured for specific light scattering and/or fluorescence parameters.

"Fixation" or "fixing" of cells refers to a chemical process that halts biochemical processes and reactions within a cell. Fixation may involve chemical crosslinking, precipitation, aggregation, and/or oxidation of molecules within the cell. In some embodiments, fixation is performed with an aldehyde. Examples of aldehydes for use as provided herein include, but are not limited to, formaldehyde, paraformaldehyde, and/or glutaraldehyde. In some embodiments, fixation is performed with an organic solvent. Examples of organic solvent for use as provided herein include, but are not limited to, methanol, ethanol, acetic acid and/or acetone. Additional examples of fixative agents that may be used in accordance with the present disclosure include, without limitation, zinc salts, mercuric chloride, chromium trioxide, picoric acid, osmium tetroxide and/or potassium dichromate. Other suitable fixatives may be used and are known in the art. In some embodiments, one or more fixative agents are used concurrently or sequentially.

"Culturing cells" refers to any method of growing or maintaining cells prior to performance of the described assay. Cell culture may be performed in any of the culture vessels known and used in the art, including coverslips, dishes, flasks, plates, and/or roller bottle suspension vessels. In some embodiments, cells are plated in multi-well plates including, but not limited to, 6-, 12-, 24-, 48-, 96-, and/or 384-well plates. The culture and/or assay surface may be glass or plastic. In some embodiments, the culture and/or assay surface is polystyrene. In some embodiments, the surface is not treated. In some embodiments, the surface may be tissue culture treated, surface treated, and/or coated with any one or more of the following non-limiting examples: collagen I, collagen IV, gelatin, poly-D-lysine, poly-L-lysine, poly-L-ornithine, fibronectin, laminin, matrigel matrix, extracellular matrix proteins, any chemically-defined synthetic molecule, and/or microporous membrane. Other suitable surfaces may be used and are known in the art.

Figure 2:
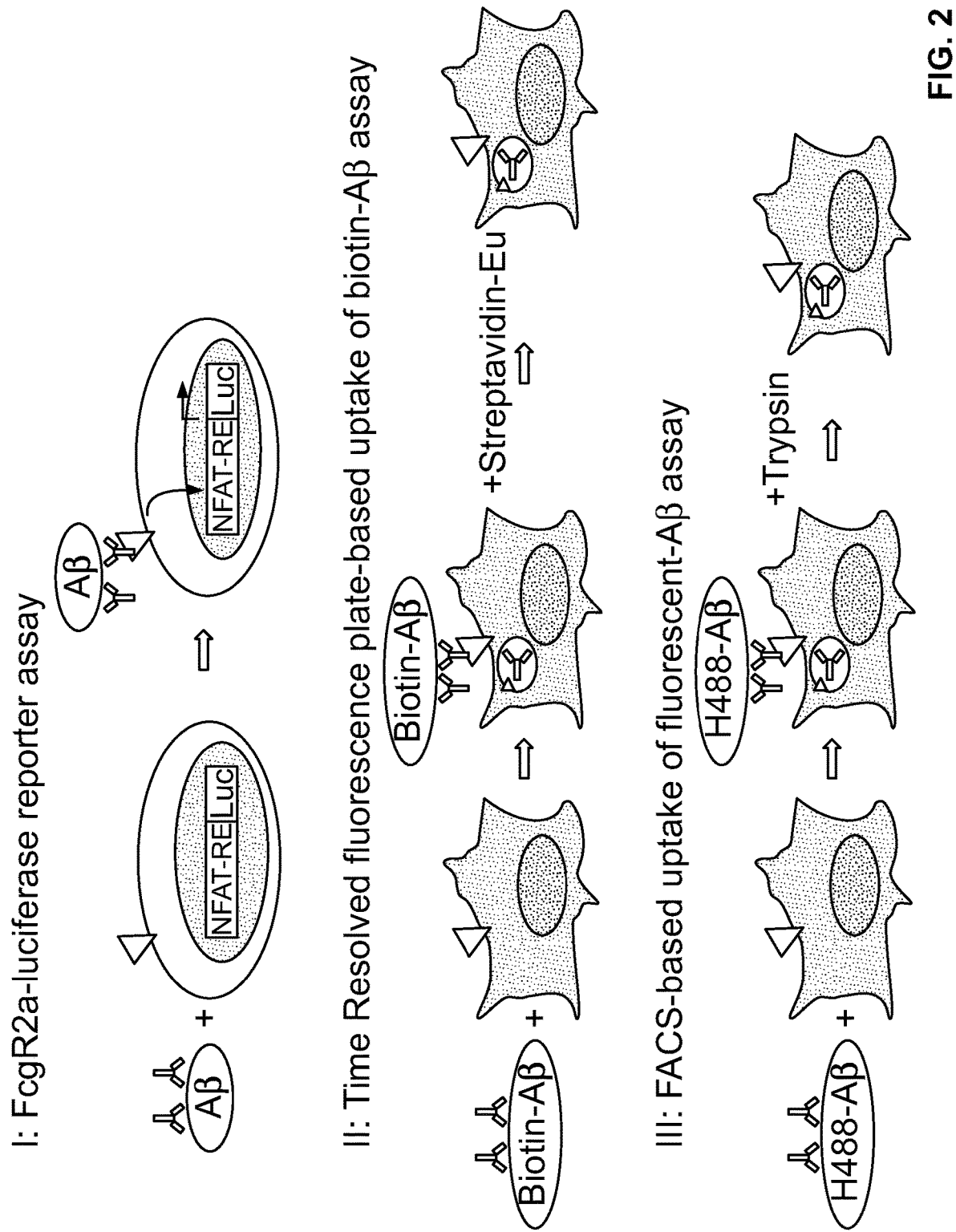
FIG. 2 depicts an exemplary schematic showing ADCP assays using (I) a FcγR2a (CD32A)-luciferase reporter, (II) time-resolved fluorescence plate-based uptake of biotinylated-Aβ, and (III) FACS-based uptake of fluorescent-Aβ.

"Permeabilizing" a cell refers to a treatment that reduces the integrity of a cell membrane, thereby allowing molecules, e.g., modifying agents, enzymes, antibodies, other proteins, access to the intracellular space (see, e.g., FIG. 2). Permeabilization may involve disrupting, dissolving, modifying, and/or forming pores in the lipid membrane. In some embodiments, permeabilization may further involve disruption of the cellular morphology or lysis of the cell. Permeabilization may be performed using any one or more of a variety of solvents, surfactants and/or commercially-available reagents. In some embodiments, the cells are permeabilized using an organic solvent. Examples of organic solvents that may be used as provided herein include, but are not limited to, benzene, n-butanol, n-propanol, isopropanol, toluene, ether, phenylethyl alcohol, chloroform, hexane, ethanol, and acetone. In some embodiments, a surfactant, detergent or emulsifying agent is used to permeabilize a cell membrane. Non-limiting examples of permeabilizing agents include saponin, NP-40, Tween-20, triton X-100, brij 35, Duponal, digitonin, thionins, chlorpromazine, imipramine, plyethyleneimine, sodium dodecyl sulfate, sodium deoxycholate, and sodium N-lauryl-sarcosylate. In further embodiments, commercially available permeabilization reagents and kits including but not limited to Leucoperm™, PerFix-EXPOSE, PerFix-nc, Fix&Perm® kit, Cytofix/Cytoperm™ solution, and Image-iT® Fixation Permeabilization Kit. Other suitable permeabilization reagents and methods may be used and are known in the art.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Description of Assays

Previously, Adolfsson et al. (2012) and Bohrmann et al. (2012) used confocal microscopy and Fleisher-Berkovich et al. (2010) used a plate reader to assay antibody-dependent cell-mediated phagocytosis of Aβ. Webster et al. (2002) used a fluorescence-activated cell sorting method to assay antibody-dependent cell-mediated phagocytosis of Aβ, which required complex data analysis, lengthy preparations, and resulted in inter- and intra-plate inconsistencies. Thus, the previous methods were inadequate for robust and high-throughput measurements of ADCP.

Provided herein are consistent, robust, and high-throughput ADCP assays that can be used to measure phagocytosis of aggregated proteins. Antibody dependent cell-mediated phagocytosis is a critical Fc effector mechanism by which antibodies can clear such proteins and the ability to reliably measure phagocytosis events mediated by antibodies is of great value.

In general, the ADCP assays provided herein are capable of reliably measuring the uptake of aggregated proteins and comprise the steps of monomerizing a protein, labeling the protein, contacting the protein with a protein-specific antibody to form an antibody-protein complex, and contacting the antibody-protein complex with a phagocytic cell to permit phagocytosis. In some embodiments, the phagocytic cell engulfs the antibody-protein complex, and the amount of internalized label is measured.

In particular embodiments, the ADCP assay comprises the steps of monomerizing a protein, fluorescently labeling the protein, contacting the protein with a protein-specific antibody to form an antibody-protein complex, and contacting the antibody-protein complex with a phagocytic cell to permit phagocytosis. In some embodiments, the phagocytic cell engulfs the antibody-protein complex, and the remaining cell surface-bound protein is digested, e.g., using trypsin. In some embodiments, the phagocytic cell is fixed, e.g., using formaldehyde. In some embodiments, the internalized fluorescence is measured, e.g., by microscopy or flow cytometry. In some embodiments, the internalized fluorescence is measured by flow cytometry, and the number or percentage of fluorescence-positive cells is determined. In some embodiments, the fluorescence signal measured from the assay is specific to phagocytosed proteins (e.g., the measured fluorescence signal is specific to internalized antibody-protein complexes). In some embodiments, the antibody binds strongly to aggregated proteins (e.g., dimeric, protofibrillar, and/or fibrillar forms of a protein) and weakly or not at all to monomeric proteins. In some embodiments, the antibody binds to monomeric proteins.

In some embodiments, the ADCP assay is used to assess the activity of an anti-Aβ antibody. For example, Aducanumab (Patel 2015; WO 2008/081008) is a fully human monoclonal IgG1 antibody that binds to soluble and insoluble aggregated forms of human Aβ, and may be assessed for ADCP activity using the provided assays. In some embodiments, the anti-Aβ antibody binds strongly to aggregated Aβ (e.g., dimeric, protofibrillar, and/or fibrillar forms of a protein) and weakly or not at all to monomeric Aβ (e.g., Gantenerumab, BAN2401, Aducanumab) thereby providing an assay specific for uptake of aggregated Aβ. In some embodiments, the anti-Aβ antibody binds to monomeric proteins as well as aggregated proteins (e.g., Bapineuzumab, Crenezumab).

In some embodiments, the ADCP assay provides consistent, accurate, and precise measurements of internalized fluorescence and phagocytic events, and also allows for high-throughput analysis.

Protein Preparation for the ADCP Assay

In some embodiments, the protein is pre-treated to improve the run-to-run consistency of the ADCP assay. For example, previous studies have used Aβ monomers reconstituted from lyophilized Aβ peptide, which produce Aβ fibrils that differ with each preparation. Variability is greatest when a large batch of Aβ fibrils are prepared and may be due to changes in the buffer composition, temperature incubation, and/or the presence of Aβ fibril/oligomer seeds.

In some embodiments, the protein preparation is treated with an agent to eliminate or reduce potential seeds and/or aggregates prior to use in assays. For example, the protein is treated with hydroxyfluoroisopropanol (HFIP) to convert aggregated peptides back to their monomeric state. HFIP-treated Aβ monomers are then used as the starting material to generate fibrils for the ADCP assay.

In some embodiments, the protein is HFIP-treated, and reconstituted in DMSO to further minimize potential seeds.

Once the monomers are generated using either of the above procedures, they are incubated for a period of time, e.g., about 4, 6, 8, 10, 12, 14, 16, 18, 20, or 24 hours, to generate a consistent preparation of fibrils for the ADCP assay. In some embodiments, the monomers are incubated for less than 48 hours to generate a consistent preparation of fibrils for the ADCP assay. In alternate embodiments, the DMSO-reconstituted monomers are frozen and stored for future use. The frozen monomers may be thawed, diluted in aqueous buffer, and/or incubated for a period of time, e.g., about 4, 6, 8, 10, 12, 14, 16, 18, 20, 24 hours, to generate a consistent preparation of fibrils for the ADCP assay. In some embodiments, the monomers are incubated for less than 48 hours to generate a consistent preparation of fibrils for the ADCP assay.

In some embodiments, monomeric proteins are incubated directly in an assay plate to form fibrils. In alternate embodiments, monomeric proteins are incubated in a tube to form fibrils and are plated after fibrilization occurs. The latter incubation may be advantageous in reducing or eliminating plate edge effects, where evaporation may affect protein concentrations and potentially, rates of Aβ aggregation.

Previous methods resulted in inconsistent assay performance when large quantities of Aβ fibrils were prepared. In some embodiments, the methods described herein provide consistent assay results regardless of the batch size prepared, e.g., whether large or small batches of Aβ monomers are prepared. In some embodiments, the methods described herein provide a heterogeneous population of fibrils and oligomers.

In some embodiments, the protein is treated, e.g., with HFIP, after being labeled for the assay. In some embodiments, the protein is treated, e.g., with HFIP, at the same time as it is labeled for the assay. In alternate embodiments, the protein is unlabeled, and an antibody that facilitates Fc-mediated phagocytosis of the protein is labeled. In some embodiments, both the protein and the antibody are labeled.

Antibody-Dependent Cell-Mediated Phagocytosis

In some embodiments, a labeled protein is contacted with a protein-specific antibody for a period of time to form an antibody-protein complex. In certain embodiments, the labeled protein is Aβ, e.g., commercially available HiLyte488 Aβ, and the antibody is an Aβ-specific antibody. In some embodiments, the Aβ-specific antibody is Aducanumab, Bapineuzumab, Gantenerumab, or Crenezumab.

In some embodiments, the antibody is an Aβ-specific antibody that binds strongly to aggregated forms of Aβ and weakly to Aβ monomers. In alternate embodiments, the antibody is an Aβ-specific antibody that binds to Aβ monomers.

In some embodiments, the antibody-protein complex, e.g., an Aducanumab-HiLyte488 Aβ complex, is contacted with a phagocytic cell for a period of time to permit phagocytosis. In some embodiments, the antibody-protein complexes are separated from non-complexed antibody and protein (e.g., by centrifugation) prior to contacting with the phagocytic cell. In alternate embodiments, the antibody-protein complexes are not manipulated prior to contacting them with cells. Performing the assay in this way increases robustness and consistency, because the antibody-protein complex is not disturbed prior to contacting it with a phagocytic cell. In one embodiment, if the phagocytic cell is an adherent cell, the cells for use in the assay are removed from plates with non-enzymatic cell dissociation buffer, and then contacted with the antibody-protein complex.

In some embodiments, antibody-protein complexes, e.g., Aducanumab/Aβ fibril complexes, are isolated by centrifugation and washing and added to phagocytic cells. In alternate embodiments, unwashed and uncentrifuged antibody-protein complexes, e.g., Aducanumab/Aβ fibril complexes, are added to phagocytic cells. Advantageously, the improvements made to the previously known assays eliminate the need for centrifugation. More specifically, in assays which employ antibodies that do not bind to monomeric forms of Ab, centrifugation is not required and the signal-to-noise ratio is increased and the ADCP assay is simplified. For example, a significant increase was observed in the Aducanumab-dependent uptake of fluorescent Aβ fibrils, from 20-40% ADCP to 60-80% ADCP, and Aducanumab-mediated ADCP reached an equilibrium plateau between 60-90 min after adding the Aducanumab/Aβ fibrils to BV-2 cells.

In some embodiments, phagocytic cells are grown, e.g., for about 1, 2, 3, 4, 5, 6 or more hours, and detached from the surface on which they are grown prior to contacting with the antibody-protein complex. In certain embodiments, the phagocytic cells are grown for less than 16 hours. In some embodiments, the phagocytic cells are frozen and stored for future use. In some embodiments, phagocytic cells are detached using an enzyme-free solution, e.g., HBSS cell dissociation buffer, to prevent Fc receptor loss. In flow cytometry, each cell that passes through and is detected by the flow cytometer is classified as a distinct "event." In previous studies of ADCP, data acquisition using flow cytometry required about 10,000 events (Webster et al., 2001). Advantageously, in some embodiments, the ADCP assay provided herein requires a smaller number of events, e.g., about 500-5000 events, thus speeding up the data acquisition process. In some embodiments, the ADCP assay provided herein uses about 500, 1000, 1500, 2000, 2500, 3000, 3500, 4000, or 5000 events.

In some instances, the antibody-protein complexes will not be completely internalized by the phagocytic cells, and some protein, antibody, and/or antibody-protein complexes may be bound to the surface of the phagocytic cell. In some embodiments, the ADCP assay further comprises eliminating or reducing surface-bound materials, e.g., antibody-protein complexes that are adhered to a cell surface but not phagocytosed by phagocytic cells. In some embodiments, the methods further comprise enzymatically removing the surface bound antibody-protein complexes. In some embodiments, the surface protein is enzymatically digested, e.g., using trypsin, following antibody-dependent cell-mediated phagocytosis. In some embodiments, the methods further comprise washing the phagocytic cells to remove extracellular protein, e.g., using a suitable buffer. In some embodiments, the surface protein is removed using non-enzymatic means, e.g., EDTA following antibody-dependent cell-mediated phagocytosis. In some embodiments, phagocytic cells are detached using an enzyme-free solution and added to antibody-fluorescently labeled protein complexes; following phagocytosis, the surface-bound protein is digested with trypsin, washed, and the number of cells with internalized fluorescent protein are determined using a flow cytometer. Exemplary phagocytic cells are described herein.

In some embodiments, the ADCP assay further comprises fixing the phagocytic cells following ADCP activity. In some embodiments, following phagocytosis, cells are incubated with trypsin, washed, and fixed using a fixative agent. Non-limiting examples of fixative agents include aldehydes such as formaldehyde, paraformaldehyde, and glutaraldehyde; organic solvents such as methanol, ethanol, acetic acid, and acetone; zinc salts; mercuric chloride; chromium trioxide; picoric acid; osmium tetroxide; and potassium dichromate. In some embodiments, one or more fixative agents are used concurrently or sequentially. In some embodiments, fixation is advantageous, because it decreases the time required to read each plate.

Cell Lines

Any suitable phagocytic cell may be used in the ADCP assay. In some embodiments, the phagocytic cells are primary cells. In other embodiments, the phagocytic cells are immortalized cells. In some embodiments, the phagocytic cells belong to an established cell line. In some embodiments, the cell is a naturally phagocytic cell, e.g., a BV-2 cell that expresses Fc receptors. In alternate embodiments, the cell is a non-naturally phagocytic cell that is engineered to express a heterologous sequence that confers phagocytic capacity, e.g., a sequence that encodes a human Fc receptor. Examples of commonly used cell lines include, without limitation, BV-2, THP-1, CHO, 293-T, 3T3, 4T1, 721, 9L, A2780, A172, A20, A253, A431, A-549, ALC, B16, B35, BCP-1, BEAS-2B, bEnd.3, BHK-21, BR293, BxPC3, C3H-10T1/2, C6, Cal-27, COR-L23, COS-7, CML T1, CMT, CT26, D17, DH82, DU145, DuCaP, EL4, EM2, EM3, EMT6/AR1, FM3, H1299, H69, HB54, HB55, HCA2, HEK-293, HeLa, Hepa1c1c7, HL-60, HMEC, HT-29, HUVEC, Jurkat, J558L, JY, K562, Ku812, KCL22, KG1, KY01, MCF-7, RBL, Saos-2, SKBR3, SKOV-3, T2, T-47D, T84, U373, U937, Vero, and J774.

In some embodiments, the phagocytic cell is a THP1 cell. The THP1 cell line is a human leukemia monocytic cell line, which expresses Fc receptors. In some embodiments, the phagocytic cell is a BV-2 cell line, which expresses Fc receptors. The BV-2 cell line is a murine microglial cell line, and microglial cells are presumed to be the main effector cells in the brain. The BV-2 cell line has been used to measure IgG-dependent uptake of Aβ fibrils (Webster et al., 2001). However, the murine BV-2 cell line may be limited by the ability to evaluate the biological activity of human antibodies, the lack of suitable reagents to assess murine Fc gamma receptors, potential inconsistency because BV-2 cells express multiple Fc receptors, and the inconsistent passage-to-passage IgG-dependent ADCP activity of the BV-2 cell line.

In an alternate embodiment, the phagocytic cell is a cell line that is engineered to expresses a human Fc receptor. In some embodiments, the phagocytic cell is a surrogate cell line that expresses a FcγR, FcαR, or FcεR receptor. In some embodiments, the phagocytic cell is a surrogate cell line that expresses a FcγR2a/CD32A receptor. In some embodiments, the phagocytic cell is a CHO cell line stably expressing human FcγR2A/CD32A (Indik et al., 1995).

In some embodiments, the phagocytic cell is a CHO-CD32A R131 cell or a CHO-CD32A H131 cell. There are two alleles of human CD32A at amino acid 131, arginine (R131) and histidine (H131). In vitro, H131 CD32A has higher affinity for human IgG1 than R131 (Shashidharamurthy et al., 2009). However, in vivo, there are inconsistent results on the improved efficacy of therapeutic monoclonal antibodies in patients with H131 or R131 alleles in CD32A (Park et al., 2012).

Cell lines engineered to expresses a human Fc receptor have several advantages: (A) they can express a single receptor, (B) they can have more stable expression of the receptor, and (C) they may be better suited for routine testing because they may be more robust and easier to grow in terms of cell maintenance. Stable cell lines have been used in other cell-based assays, e.g., the murine cell line NB41A3 that expresses human GFRalpha3 for the NBN KIRA assay, and the Jurkat cell line expressing human CD16A to measure ADCC activity (Schlee et al., 2006; Parekh et al., 2012).

In one embodiment, if the phagocytic cell is an adherent cell, cells are removed from surfaces with non-enzymatic cell dissociation buffer, and applied to the antibody-protein complex.

Antibody-mediated uptake of aggregated proteins, e.g., by CHO-CD32A cells, leads to internalization of the proteins. In some embodiments, the ADCP assay further comprises eliminating or reducing non-specific binding of protein to the surface of phagocytic cells. In some embodiments, a scavenger inhibitor, e.g., fucoidan, is used to eliminate or reduce antibody-independent internalization of a protein. Scavenger receptors are capable of antibody-independent internalization of Aβ fibrils and can prevent dose-dependent Aducanumab-mediated uptake of Aβ fibrils. Non-specific protein binding can be prevented by blocking scavenger receptors on the surface of the cells. Blocking of scavenger receptors can be achieved by treatment of cells with pharmacological inhibitors including, but not limited to, fucoidan, polyinosinic acid, and dextran sulfate. In some embodiments, methods provided herein comprise contacting phagocytic cells with fucoidan. In some embodiments, phagocytic cells are contacted with fucoidan before they are contacted with an antibody-protein complex. Other suitable blocking agents that eliminate or reduce non-specific binding of protein to the surface of phagocytic cells may be used and are known in the art.

Previous ADCP assays required the use of a scavenger inhibitor, and were also limited in the cell types that could be used. For example, Webster et al. (2001) was limited to the BV-2 murine microglia cell line and required fucoidan-mediated scavenger inhibition. In contrast, the cell lines described herein can internalize Aβ fibrils in an antibody dose dependent manner irrespective of the presence or absence of fucoidan. Thus, advantageously, scavenger receptor inhibitors need not be used with the ADCP assay provided herein. In some embodiments, a scavenger inhibitor is not required for dose-dependent antibody-mediated uptake of fibrils.

In some embodiments, the phagocytic cell line is stable after about 10, 20, 30, 40, 50, 60, 70, 80, or more passages.

Flow Cytometry

In some embodiments, the amount of antibody-protein complex internalized by phagocytic cells can be determined using flow cytometry. In some embodiments, the amount of antibody-protein complex internalized by phagocytic cells can be determined using FACS. In some embodiments, the flow cytometer is a sheath-flow cytometer. In alternate embodiments, the flow cytometer is a flow-cell cytometer. For example, the Guava cytometer is a flow-cell cytometer in which a microcapillary flow cell eliminates the need for sheath fluid and is capable of counting the absolute number of cells. In some embodiments, the amount of antibody-protein complex internalized by phagocytic cells can be determined using Guava flow cytometry. In some embodiments, the amount of antibody-protein complex internalized by phagocytic cells can be determined using fluorescence microscopy.

In an alternate embodiment, the amount of antibody-protein complex internalized by phagocytic cells can be determined with a plate reader. Plate readers are designed to detect biological, chemical, or physical events of samples, and common detection modes for microplate assays are absorbance, fluorescence intensity, luminescence, time-resolved fluorescence, and fluorescence polarization. In yet another alternate embodiment, the amount of antibody-protein complex internalized by phagocytic cells can be determined using a biotin-streptavidin-based method. In other embodiments, the internalized antibody-protein complex can be assessed by microscopy, permitting visualization of intracellular events. Advantageously, the FACS-based methods provided herein exhibit superior signal-to-noise, increased consistency, and/or decreased inter- and intra-plate variability as compared to the plate reader-based and the biotin-streptavidin-based methods. In addition, the FACS-based methods allow for high-throughput analysis of ADCP.

In some embodiments, an antibody is incubated with about 1%, 3%, 5%, 10%, 15%, 20%, 25%, or more labeled protein. For example, Aducanumab is incubated with about 1%, 3%, 5%, 10%, 15%, 20%, 25%, or more labeled Aβ fibrils. In some embodiments, the label is a detectable label selected from a tag, a protein modification, a dye, radioactive dye, an enzyme, a fluorophore, a chromophore, a metal colloid, a chemilluminescent molecule, a bioluminescent molecule, a histidine tag, a GST tag, a FLAG tag, a MBP tag, a sulfoindocyanine Cy dye, 3H, 32P, 35S, 125I, 14C, europium, horseradish peroxidase, penicillinase, alkaline phosphatase, FITC, rhodamine, fluorescein, Lucifer yellow, HiLyte, green fluorescent protein, red fluorescent protein, and Alexa fluorophores. In certain embodiments, the protein is Aβ and fluorescently labeled, e.g., commercially available HiLyte488 Aβ. In certain embodiments, the antibody binds labeled and unlabeled proteins with similar affinity.

Data acquisition using flow cytometers typically takes longer as compared to traditional plate readers, creating several logistical challenges to the use of flow cytometry for high-throughput measurements. First, flow cytometry would be expected to limit the number of plates that could be run in a day. Second, an extended read time could result in a difference in signal from the first to last acquired well. As described above, in some embodiments, the ADCP assay further comprises fixing the phagocytic cells following ADCP activity, thereby decreasing the time to read each plate.

In flow cytometry, each cell that passes through and is detected by the flow cytometer is classified as a distinct "event." In some embodiments, each type of light that is detected by the flow cytometer (e.g., forward-scatter, side-scatter, each wavelength of fluorescence emission) is assigned its own channel. Thus, flow cytometry data may plot each event and represent the signal intensity of light detected in each channel for each event.

In some embodiments, standards, controls, and samples are assayed, and control cells are used to adjust settings for the flow cytometer during data acquisition. In some embodiments, the standards, controls, and/or samples are run in singlet, duplicate, triplicate, or more. In some embodiments, replicates are averaged for subsequent analysis.

In some embodiments, the measured cells may be plotted using a histogram graph with fluorescent signal on the x-axis and the number of cells on the y-axis. In some embodiments, the analysis provides a binary output of fluorescence-positive cells. In some embodiments, ADCP activity and internalized fluorescence is analyzed as a number or percentage of fluorescence-positive cells. Analyzing percent fluorescence is more robust, consistent, and sensitive than previous methods, which had analyzed mean fluorescence intensity (see, e.g., Webster et al. 2001). In some embodiments, the percentage of fluorescence-positive cells (+FITC cells) is calculated by using a gate to the right of unstained cells. In some embodiments, the % ADCP (% fluorescent positive (+) cells/total cells) is calculated from the cells acquired and can be plotted against antibody concentration. By using the % ADCP cells, spurious results obtained using mean fluorescence intensity can be avoided. In some embodiments, the data are analyzed by a parallel line analysis (PLA) software package. In some embodiments, the relative potency of each sample is calculated. Other suitable methods of measuring fluorescence may be used and are known in the art.

In a specific embodiment, lyophilized, HFIP-treated, DMSO-solubilized 10% labeled-HiLyte488-Aβ monomers are incubated to form Aβ fibrils in a tube at 37° C. while shaking overnight. Next, Aβ fibrils are transferred, e.g., to wells in a 96-well plate. Dilutions of Aducanumab standard, control, and samples are added to wells containing Aβ fibrils and incubated with shaking at 37° C. for 1 hour to form Aducanumab-Aβ complexes. Non-enzymatically detached CHO-CD32A H131 cells are added to the plate (e.g., 60,000 cells/well) and incubated at 37° C. with 5% $CO_2$ for 2 hours to permit ADCP activity. Following ADCP, trypsin is added to the wells to digest any cell surface-bound Aβ fibrils and to detach adhered cells from the plate surface. Cells are washed and fixed, e.g., using formaldehyde. The internalized fluorescence is measured, e.g., the plate is run on a Guava flow cytometer.

REFERENCES

Ackerman et al., 2013. Enhanced phagocytic activity of HIV-specific antibodies correlates with natural production of immunoglobulins with skewed affinity for FcγR2a and FcγR2b. J. Virol. 87, 5468.
Bohrmann et al., 2012. Journal of Alzheimer's Disease 28, 49-69. Gantenerumab: A Novel Human Anti-Aβ Antibody Demonstrates Sustained Cerebral Amyloid-β Binding and Elicits Cell-Mediated Removal of Human Amyloid-β.
Burstein et al., 2013. Safety and pharmacology of ponezumab (PF-04360365) after a single 10-minute intravenous infusion in subjects with mild to moderate Alzheimer disease. Clin Neuropharmacol. 2013 January-February; 36(1):8-13. PMID: 23334069.
Ferreira et al., 2011. Neuropeptide Y inhibits interleukin-1b-induced phagocytosis by microglial cells, J Neuroinflammation 8:169.
Gallo et al., 2010. The influence of IgG density and macrophage Fc (gamma) receptor cross-linking on phagocytosis and IL-10 production. Immunol. Lett. 133, 70.
Horton et al., 2010. Fc-engineered anti-CD40 antibody enhances multiple effector functions and exhibits potent in vitro and in vivo antitumor activity against hematological malignancies. Blood, 116, 3004.
Indik et al., 1995. The molecular dissection of Fc gamma receptor mediated phagocytosis. Blood 86: 4389-4399.
Lundholt et. al., 2003. A simple technique for reducing edge effect in cell-based assays. J Biomolecular Screening 566-570.
Oflazoglu et al., 2009. Macrophages and Fc-receptor interactions contribute to the antitumor activities of the anti-CD40 antibody SGN-40. Br. J. Cancer, 100, 113.
Park et al., 2012. Genetic Polymorphisms of FcgRIIa and FcgRIIIa are not predictive of clinical outcomes after cetuximab plus irinotecan chemotherapy in patients with colorectal cancer. Oncology 82(2): 83-9.
Parekh et al., 2012. Development and validation of an antibody-dependent cell-mediated cytotoxicity-reporter gene assay. mAbs 4:3, 310-318.
Patel. Biogen's aducanumab raises hope that Alzheimer's can be treated at its source. Manag Care. 2015 June; 24(6):19. PubMed PMID: 26182718.
Richards et al. Optimization of antibody binding to FcgammaRIIa enhances macrophage phagocytosis of tumor cells. Mol. Cancer. Ther. 7, 2517.
Selvaraj et al., 1988. The major Fc receptor in blood has a phosphatidylinositol anchor and is deficient in paroxysmal nocturnal haemoglobinuria. Nature 33
Schlee et al., 2006. Quantitative analysis of the activation mechanism of the multicomponent growth-factor receptor Ret. Nature Chemical Biology 11: 636-644.
Shashidharamurthy et al., 2009. Dynamics of the interactions of Human IgG subtype immune complexes with cells expressing R and H allelic forms of a low-affinity Fcγ Receptor CD32A. J Immunol 183: 8216-8224.
Ulvestad et al., 1994. Fc receptors for IgG on cultured human microglia mediate cytotoxicity and phagocytosis of antibody-coated targets. J Neuropathol Exp Neuro, 53 (1): 27-36.
Vieth et al., 2010. Differential requirement of lipid rafts for FcgRIIA mediated effector activities. Cell Immunol. 265 (2): 111-110.
Webster et al., 2001. Antibody-Mediated Phagocytosis of the Amyloid b-peptide in microglia is differentially modulated by C1q. J Immunol 166: 7496-7503.
Zhang et al., 2010. Coordination of Fc receptor signaling regulates cellular commitment to phagocytosis. Proc. Natl. Acad. Sci. USA. 107, 19332.

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Example 1

Evaluating ADCP Assay Formats

In order to develop a robust and accurate ADCP assay, several different methods were evaluated. First, an FcγR2a/CD32A reporter gene cell line from Promega was assessed (FIG. 2, I). Fcγ receptor reporter cell lines have been shown to be robust, accurate and precise surrogate assay systems to measure Fab and Fc activities of antibodies (Parekh et al., 2012). A fully human monoclonal IgG1 antibody, Aducanumab, was used in the ADCP assays. Aducanumab targets aggregated forms of Aβ with high affinity. Aducanumab/Aβ complexes were added to FcγR2a-expressing Jurkat cells which contain an NFAT-luciferase (luc) reporter gene. Aducanumab/Aβ binds to FcγR2a and activates the NFAT-Luc pathway. After 5-24 h, luminescence is read on a plate reader. The signal to noise measured was very low compared to a positive control (Promega), and therefore, this format was not used for further analysis.

Second, a time-resolved fluorescence assay format that measures internalization of biotinylated-Aβ was assessed (FIG. 2, II). Aducanumab/biotinylated-Aβ complexes were added to a phagocytic murine BV-2 cell line. After phagocytosis, internalized biotinylated-Aβ was measured by permeabilizing cells and adding streptavidin-Europium (Eu). Time-resolved fluorescence was read on a plate reader. Variability and inconsistent data were observed from plate to plate, and therefore, this format was not used for further analysis.

Third, a FACS-based method was used to assess the ADCP activity of Aducanumab (FIG. 2, III). Aducanumab/fluorescently-labeled Aβ complexes were added to BV-2 cells. After phagocytosis, surface-bound Aβ was digested with trypsin and % cells with internalized fluorescent Aβ were counted using a flow cytometer. Consistent inter- and intra-plate accuracy and precision and a high signal-to-noise ratio were observed using this format, which then served as the basis for further analysis.

Example 2

Flow Cytometry

Several reagents used in the assay were characterized. 10% HiLyte488 Aβ monomers were mixed with 90% unlabeled Aβ monomers and polymerized overnight while shaking at 37° C. to make Aβ fibrils. First, it was demonstrated that fluorescent (HiLyte488) Aβ fibrils could be bound similarly by Aducanumab as unlabeled Aβ fibrils (data not shown). Second, flow cytometry was used to demonstrate that the BV-2 microglial cell line express Fc receptors (data not shown).

Figure 3:
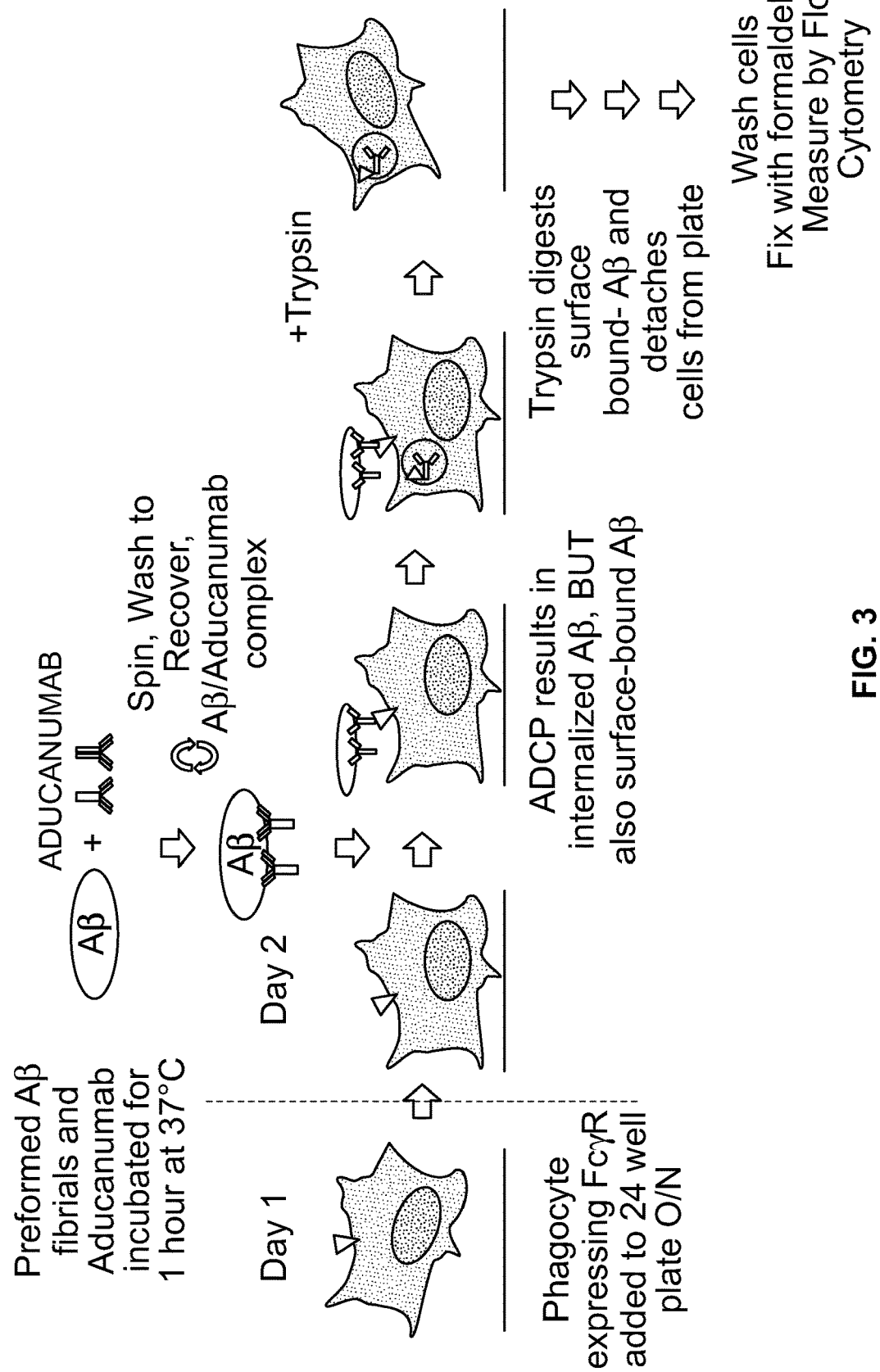
FIG. 3 depicts an exemplary schematic of an ADCP assay. BV-2 cells are added to tissue culture plates and incubated overnight to allow for cell attachment. The following day Aβ fibrils are incubated with various concentrations of Aducanumab for 30-60 minutes at 37° C. and then spun and washed to recover the Aβ/Aducanumab complex. Next, the AB/Aducanumab complex is added to the wells containing adherent BV-2 cells and incubated at 37° C. to start the ADCP assay. After the ADCP incubation, excess Aβ/Aducanumab complex in the cell medium is removed and the cells are gently washed with PBS. Extracellular Aβ/Aducanumab is digested by addition of trypsin and incubation for 20 min at 4° C. Following trypsin digestion, the cells are spun and washed twice. To detect the Aducanumab-mediated intracellular AB, fluorescent cells are counted in a flow cytometer.

Microglial BV-2 cells were first allowed to adhere to tissue culture plates overnight (FIG. 3). Next, Aducanumab was incubated with 10% HiLyte488 Aβ fibrils. After this incubation, Aducanumab/Aβ fibril complexes were isolated with several centrifugation and wash steps and added to the adherent BV-2 cells. Following ADCP, trypsin was added to detach adherent cells and digest any cell surface-bound Aβ fibrils. Following several washes to remove extracellular Aβ, cells containing internalized fluorescent Aβ fibrils were read using a flow cytometer. The measured fluorescent cells were plotted using a histogram graph with fluorescent signal on the x-axis and the number of cells on the y-axis. The % fluorescent positive cells (+FITC cells) were calculated by using a gate to the right of unstained cells.

In an alternate embodiment, the centrifugation and wash steps to prepare and isolate Aducanumab/Aβ fibril complexes were removed. After 30 min incubation of Aducanumab and Aβ fibrils, the complete, un-centrifuged mixture was added to wells containing BV-2 cells. This new format resulted in a significant increase in the Aducanumab-dependent uptake of fluorescent Aβ fibrils, from 20-40% ADCP to 60-80% ADCP (data not shown). Using this format, Aducanumab-mediated ADCP reached an equilibrium plateau between 60-90 min after adding the Aducanumab/Aβ fibrils to BV-2 cells. This new format increased the signal-to-noise ratio and simplified the assay.

In an alternate embodiment, adherent cells are detached with an enzyme free solution to prevent receptor loss, and added to the Aducanumab/Aβ fibril complexes, instead of detaching the cells and allowing them to adhere overnight before the assay is performed. This new format increases the assay robustness since it has been shown that cells may behave differently depending on their position in a plate. This phenomenon is described as an edge effect, where cells can grow differently on the outer wells of plates (Lundholt el al).

Figure 4:
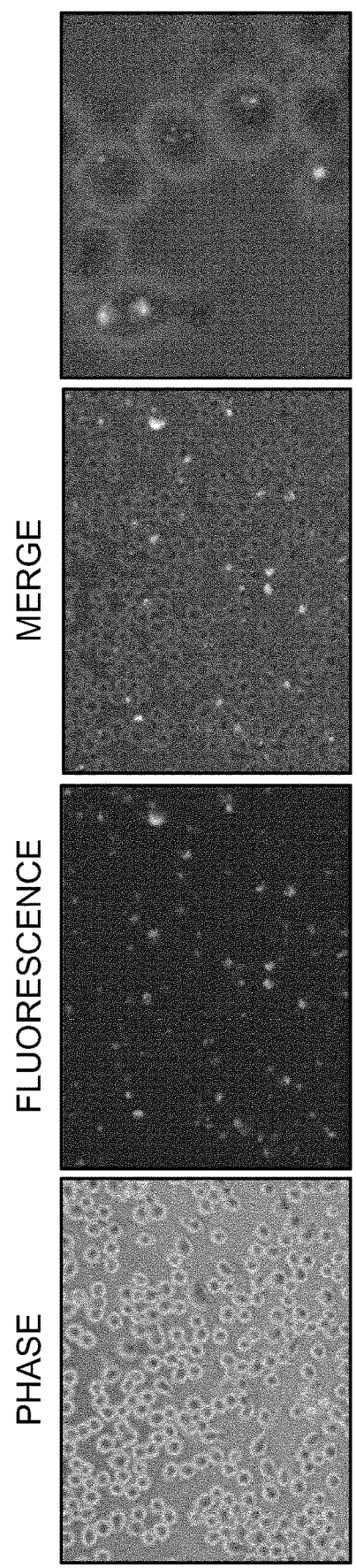
FIG. 4 depicts fluorescent microscopy images of Aducanumab-mediated internalization of fluorescent Aβ by BV-2 cells (HiLyte488(H488)-Aβ fibrils in the presence of 0.5 µM Aducanumab and BV-2 cells). Fluorescent and phase contrast images were taken after the ADCP assay. The images were overlayed to create a merge image. A portion of the image was magnified to more clearly depict the fluorescent punctate structure seen in BV-2 cells in the presence of Aducanumab.

To corroborate the flow cytometry assays, Aducanumab-mediated fluorescent Aβ internalization was assessed by fluorescence microscopy (FIG. 4). Fluorescent Aβ fibrils were added to BV-2 cells in the presence of Aducanumab. Fluorescent and phase contrast images show that Aducanumab mediated the uptake of Aβ by BV-2 cells as shown by the presence of punctate fluorescent structures. Confocal microscopy confirmed that fluorescence was not observed on the plasma membrane of the cells, suggesting that fluorescent Aβ is intracellular (data not shown).

In one embodiment, following the final wash step, cells were fixed with formaldehyde. Data acquired immediately after fixation was compared with data acquired from plates fixed in formaldehyde and stored at 4° C. overnight. Dose response curves comparing fresh vs. overnight cells were similar. These experiments decreased the time required to read each plate and allowed for data to be acquired one day after the assay had been completed.

Figure 6A:
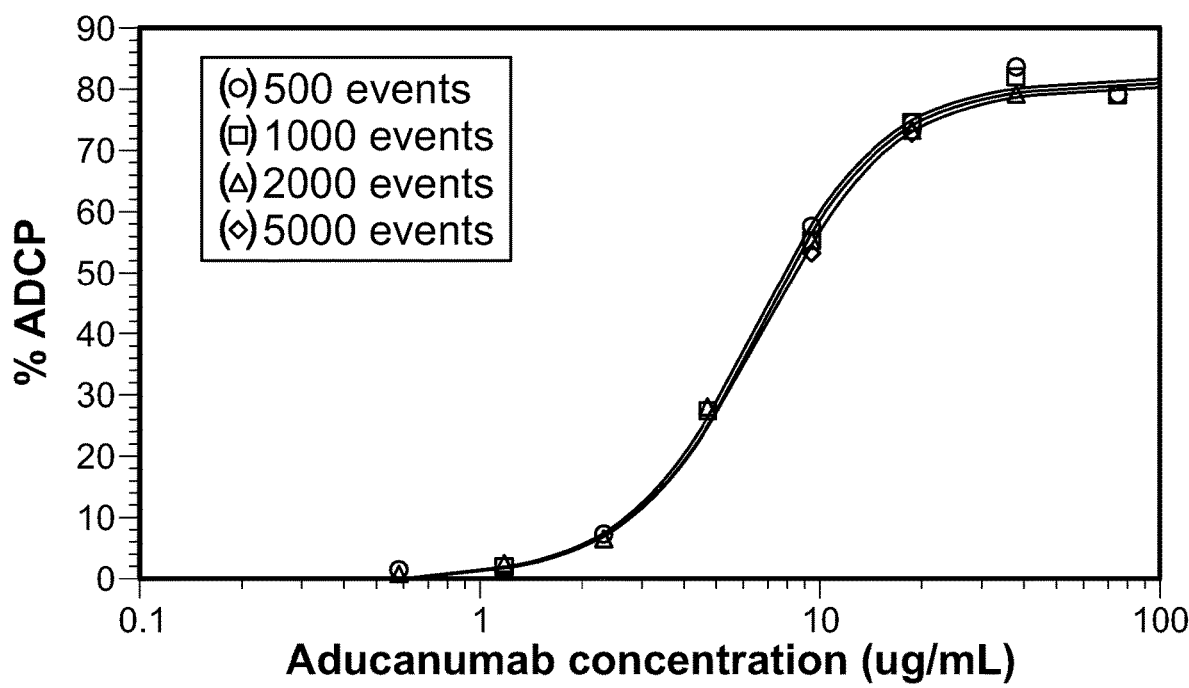
FIG. 6A is a graph showing an assessment of assay simplification parameters. 500, 1000, 2000, and 5000 cells (events) were counted and compared in the ADCP assay.
Figure 6B:
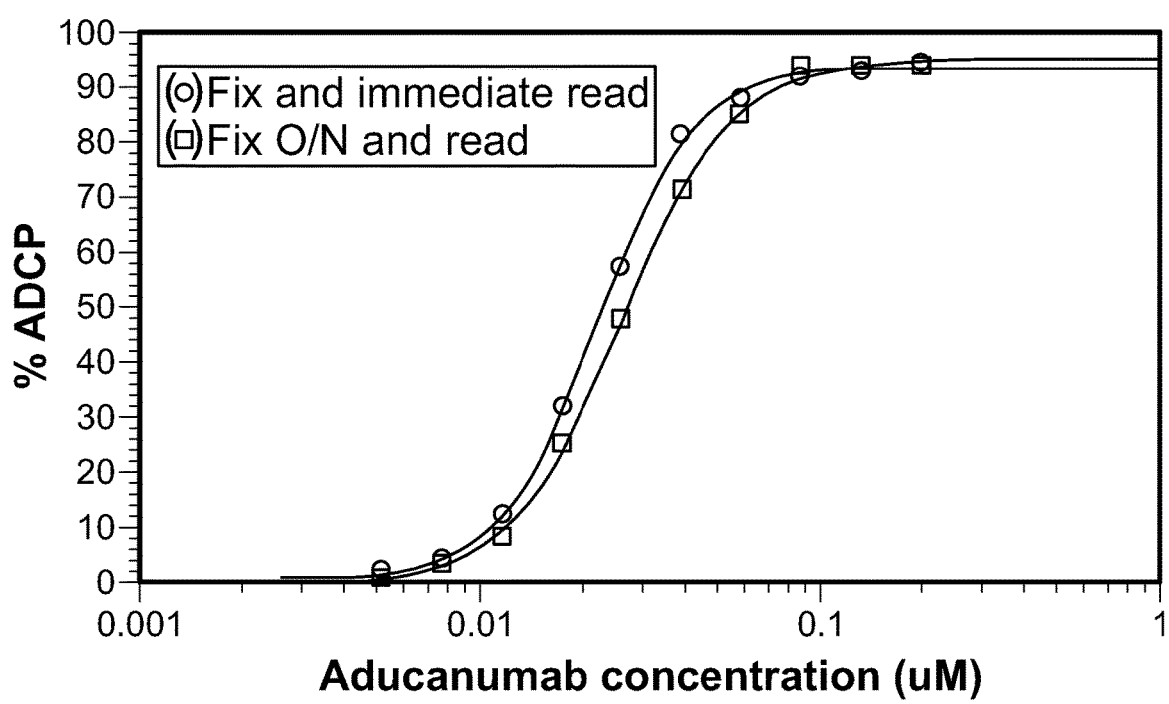
In FIG. 6B, the ADCP assay was compared using cells that were formaldehyde-fixed and read immediately or cells that had been fixed and stored at 4° C. overnight.

Data acquisition using flow cytometers takes longer to read a full plate than traditional plate readers. This issue created several logistical challenges to the routine use of flow cytometry. First, this could limit the number of plates that could be run in a day. Second, an extended read time could result in a difference in signal from the first to last acquired well. Several experiments were performed to solve or mitigate these challenges. The number of events acquired using the Guava flow cytometer was assessed to determine whether a smaller number of events could be read to speed up the read process. It was determined that 500, 1000, and 2000 events was similar to acquiring 5000 events (FIGS. 6A, B).

Example 3

Evaluating Cell Lines

Several cell lines were assessed for their ability to promote Aducanumab-mediated ADCP of Aβ fibrils. The BV-2 cell line is a murine microglial cell line used to measure Aducanumab's phagocytosis of Aβ fibril activity. Microglial cells are presumed to be the main effector cells in the brain. The BV-2 cell line has been used to measure IgG-dependent uptake of Aβ fibrils (Webster et al., 2001). However, one potential challenge to using the BV-2 cell line may be the use of a murine cell line and murine Fc gamma receptors to assess the biological activity of a human antibody. A second challenge may be the lack of suitable reagents to assess murine Fc gamma receptors. A third challenge may be the consistency of ADCP activity, because the BV-2 cell line expresses multiple Fc receptors.

One alternative approach to the murine BV-2 cell line is the use of a surrogate cell line that stably expresses a human Fc receptor. Stable cell lines have been used in other cell-based assays, e.g., the murine cell line NB41A3 that expresses human GFRalpha3 for the NBN KIRA assay, and the Jurkat cell line expressing human CD16A to measure ADCC activity (Schlee et al., 2006; Parekh et al., 2012). These surrogate cell lines have several advantages: (A) they can express a single receptor, (B) they can have more stable expression of the receptor, and (C) they may be better suited for routine testing because they may be more robust and easier to grow in terms of cell maintenance.

A CHO cell line stably expressing human FcγR2A/CD32A was used as a potential model system to assess the consistency of Aducanumab-mediated ADCP activity in vitro. Expression of human FcγR2A/CD32A is sufficient to render a non-phagocytic cell into a cell capable of mediating Fc-dependent uptake of opsonized particles and acidification of phagocytosed compartments (Indik et al., 1995). Several experiments were performed to compare BV-2 and a CHO cell line stably expressing CD32A in measuring Aducanumab-mediated uptake of Aβ fibrils. The CHO-CD32A cell line exhibited more robust and consistent Aducanumab-mediated ADCP activity. The CHO-CD32A cell line yielded a more robust and consistent dose response curve as compared to the BV-2 cell line.

The Aducanumab ADCP assay was converted from a 24 well assay, where the flow cytometry was performed on a Becton Dickinson FACS caliber (BD FACS), to a 96 well assay, which was performed on a Guava cytometer. The CHO-CD32A cell line showed more robust and consistent dose dependent ADCP activity when comparing assays between flow cytometers and between different days. In contrast, the shape of the BV-2 cell line dose response curves varied from day to day.

Figure 5A:
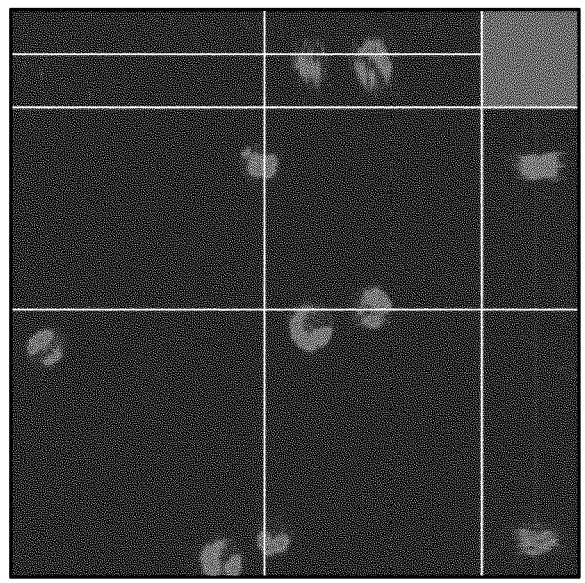
FIG. 5A shows confocal microscopy image of CHO-CD32A cells in the presence of H488-Aβ fibrils and no Aducanumab.
Figure 5B:
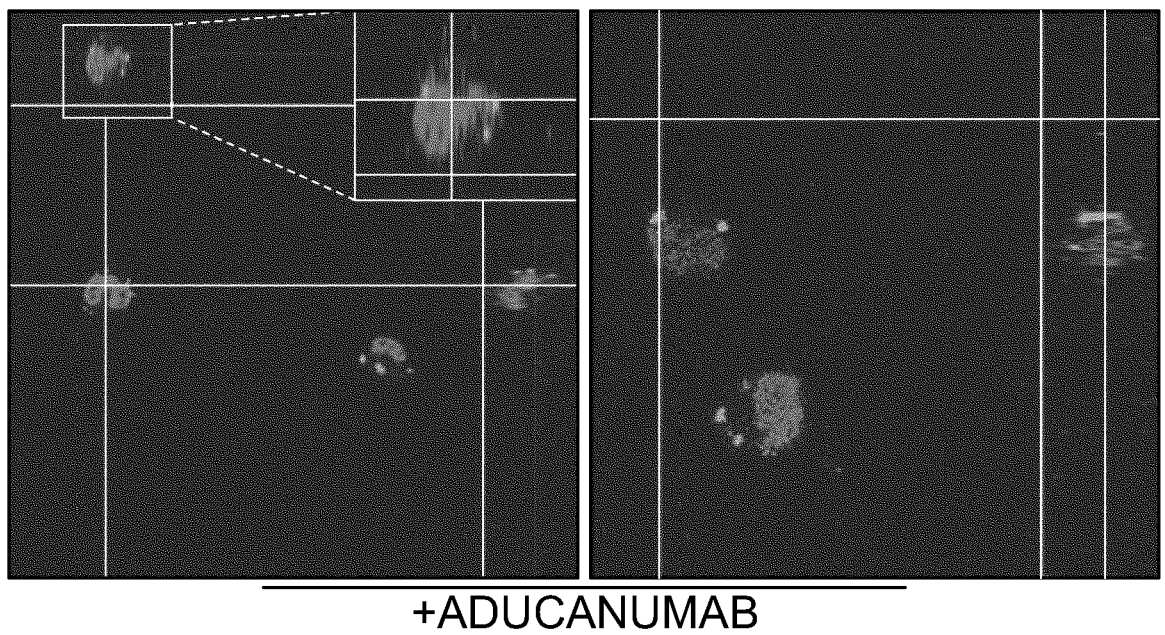
FIG. 5B shows confocal microscopy image of CHO-CD32A cells in the presence of H488-Aβ fibrils and Aducanumab. The inset is a magnified image of a 3D-reconstructed CHO-CD32A cell containing internalized fluorescent Aβ punctate structures.
Figure 5C:
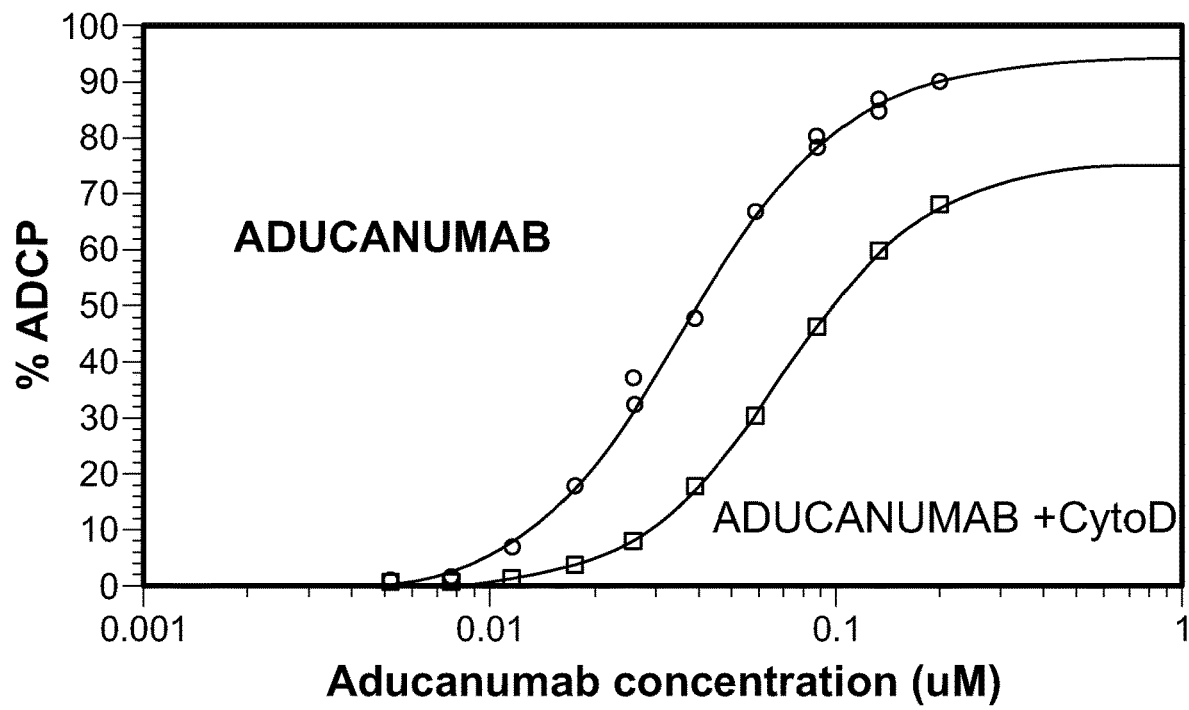
FIG. 5C shows the CHO-CD32A ADCP assay performed in the presence of cytochalasin D.
Figure 5D:
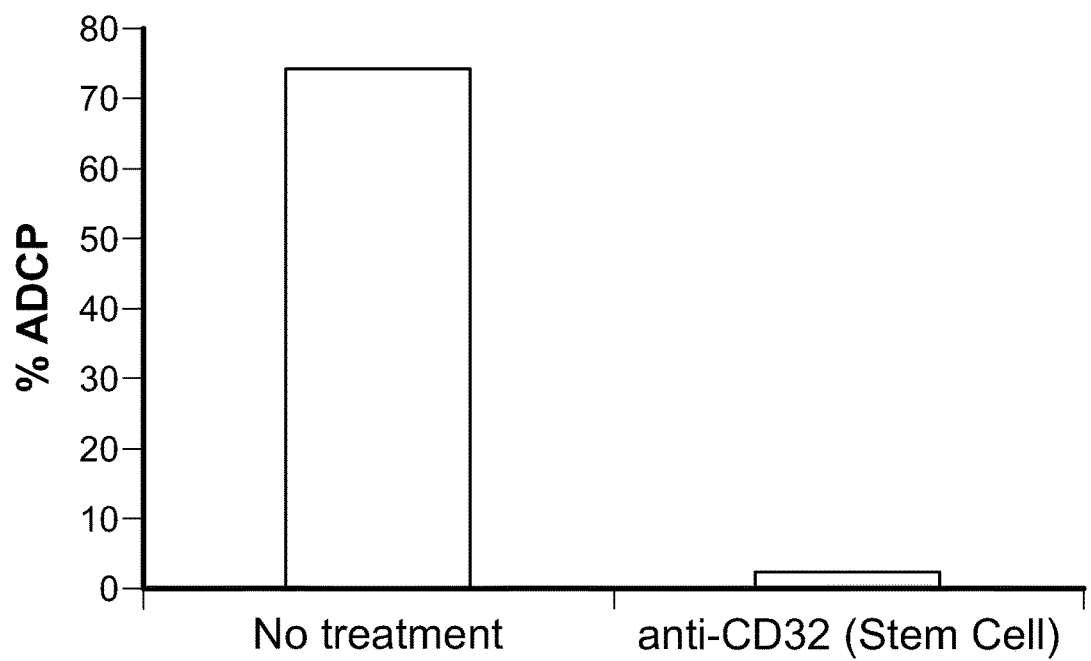
FIG. 5D shows the CHO-CD32A ADCP assay performed in the presence of an anti-CD32 blocking antibody.

To assess the CHO-CD32A cell line for use in measuring Aducanumab's ADCP activity, a panel of assays was performed to demonstrate that the signals measured by flow cytometry were specific to internalized Aβ and dependent on the presence of CD32. First, confocal microscopy experiments demonstrated that Aducanumab-mediated uptake of Aβ fibrils into CHO-CD32A cells led to internalized Aβ fibrils (FIGS. 5A-D). Fluorescent punctate structures were visualized inside of the cell and only observed in the presence of Aducanumab (FIGS. 5A,B). Second, Aducanumab-mediated ADCP in CHO-CD32A cells could be inhibited by the actin polymerization inhibitor, Cytochalasin D (FIG. 5C). Third, Aducanumab-mediated ADCP could be inhibited by blocking antibodies against CD32A (FIG. 5D).

The scavenger receptor inhibitor fucoidan was used to inhibit binding of Aβ fibrils to the scavenger receptor on the microglial BV-2 cell line. The scavenger receptor is capable of antibody-independent internalization of Aβ fibrils and can prevent dose-dependent Aducanumab-mediated uptake of Aβ fibrils. The CHO-CD32A cell line could internalize Aβ fibrils in an Aducanumab-dose dependent manner irrespective of the presence or absence of fucoidan (data not shown). Thus, fucoidan was omitted from further CHO-CD32A ADCP protocols.

There are two alleles of human CD32A at amino acid 131, arginine (R131) and histidine (H131). In vitro, H131 CD32A has higher affinity for human IgG1 than R131 (Shashidharamurthy et al., 2009). However, in vivo, there are inconsistent results on the improved efficacy of therapeutic monoclonal antibodies in patients that have the H131 vs. R131 alleles in CD32A (Park et al., 2012). CHO-CD32A H131 was used for further analysis.

Example 4

Forming Aβ Fibrils

The formation of Aβ fibrils used in the Aducanumab ADCP assay is critical for robust and reproducible measurements of Aducanumab-mediated ADCP activity. Previously, Webster et al. used Aβ monomers reconstituted from lyophilized Aβ peptide. In one embodiment, Aβ monomers in aqueous buffer were converted to Aβ fibrils by incubation overnight at 37° C. while shaking (row 1 in FIG. 7). Next, the Aβ fibrils were aliquoted and frozen at −70° C. On the day of the experiment, Aβ fibrils were thawed and opsonized with Aducanumab prior to addition to adherent cells. Although this procedure resulted in Aβ fibrils that could be used in the assay, this procedure resulted in Aβ fibrils which differed from one preparation to another. This variability was greatest when a large batch of Aβ fibrils were prepared. This variability may be due to changes in the buffer composition, temperature incubation, and/or small amounts of Aβ fibril/oligomer seeds that may have been present at the start of the fibrillization.

To minimize the amount of potential seeds in the starting Aβ monomer preparation, hydroxyfluoroisopropanol (HFIP)-treated Aβ monomers were selected as the starting material to make Aβ fibrils. HFIP treatment results in conversion of aggregated peptides/proteins back to their monomeric state.

Figure 7:
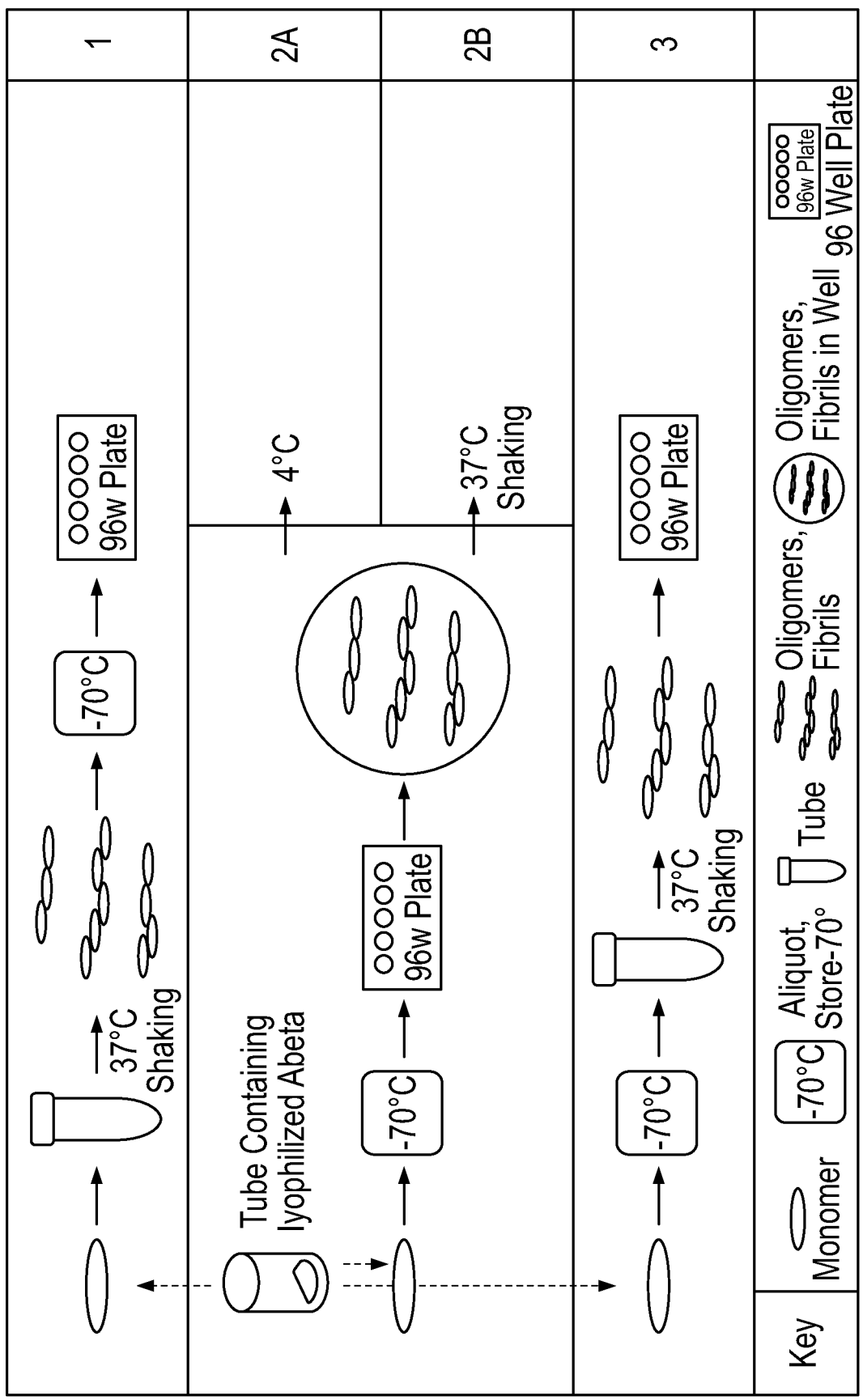
FIG. 7 depicts an exemplary schematic of different protocols to create AB fibrils and use in the ADCP assay (protocols 1, 2A, 2B, and 3)

Several alternative protocols were assessed to increase the consistency of the Aβ fibril performance in the Aducanumab ADCP assay (rows 2A, 2B, and 3 in FIG. 7). Lyophilized HFIP-treated Aβ peptide was reconstituted in DMSO to further minimize the amount of potential Aβ seeds in the reconstituted starting material. These DMSO-reconstituted Aβ monomers were aliquoted and frozen at −70° C. On the day prior to the experiment, the monomers were thawed, diluted into aqueous buffer, plated into 96-well plates, sealed, and incubated overnight under different conditions.

In protocol 2A, the plates were incubated at 4° C., which is similar to the conditions used in the Aducanumab competition Aβ binding assay. Protocol 2A did not yield a sigmoidal dose response curve with a high signal-to-noise ratio (data not shown). In protocol 2B, the plates were incubated at 37° C. while shaking, which is most similar to protocol 1. Protocol 2B yielded a sigmoidal dose response curve with a high signal-to-noise ratio (data not shown). Protocol 2B also resulted in more consistent Aβ performance in the Aducanumab ADCP assay. A large batch of DMSO Aβ monomers was comparable to smaller batches of DMSO Aβ monomers using Protocol 2B. The production of a large batch of this critical reagent was a key part of this method development and qualification.

Plate uniformity experiments were performed using protocol 2B. These experiments demonstrated that there were differences in the ADCP activity of the Aβ fibrils on the edges of the plate, especially in row H (Table 1 Panel A). This may be due to evaporation at the plate edges, potentially resulting in higher concentrations of Aβ fibrils. This plate effect could also be seen in experiments using only the inner 60 wells of a 96 well plate (Table 1 Panel B; see Row B compared to Rows C-G).

TABLE 1

Exemplary performance using protocol 2B

A

|  |  | 1 | 2 | 3 | 4 | 5 | 6 | 7 | 8 | 9 | 10 | 11 | 12 |
|---|---|---|---|---|---|---|---|---|---|---|---|---|---|
| 75 µg/mL BART | A | 71.8 | 71 | 73.1 | 72.4 | 72.6 | 68.6 | 71 | 69.3 | 68.1 | 69.4 | 69.8 | 1.2-CNTL |
|  | B | 67.8 | 66.7 | 68.3 | 66.2 | 68.3 | 68.1 | 64.8 | 69.1 | 67 | 63.6 | 62.3 | 62.3 |
|  | C | 64.5 | 66.3 | 63.4 | 66.9 | 67.3 | 64.4 | 64.9 | 68.3 | 67.2 | 64.3 | 66.2 | 55 |
|  | D | 70.1 | 71.6 | 69.1 | 68.3 | 68.9 | 65.3 | 65.6 | 68 | 65.3 | 67.2 | 63.1 | 62.2 |
|  | E | 63.7 | 66.7 | 67.4 | 64 | 65.7 | 65.6 | 65.3 | 66.2 | 65.1 | 59.2 | 62.9 | 57.8 |
|  | F | 61.1 | 66.2 | 69.3 | 65.6 | 66.3 | 64.5 | 66.7 | 63.2 | 64.8 | 62.9 | 60.1 | 61.1 |
|  | G | 50.3 | 63.2 | 66.3 | 67.1 | 64.3 | 67.5 | 65.2 | 62.5 | 63.1 | 61.8 | 60.4 | 59.8 |
|  | H | 56.9 | 61.3 | 62.4 | 63.7 | 66.1 | 63.4 | 62.5 | 63.3 | 59.9 | 58.1 | 62.1 | 55.4 |
| 4.7 µg/mL BART | A | 58.2 | 53.9 | 53.8 | 57.8 | 54.1 | 59.4 | 53.8 | 57.3 | 52.5 | 54.8 | 58 | 2.3-CNTL |
|  | B | 52.3 | 48.3 | 49.6 | 48.4 | 50.2 | 52.3 | 49.1 | 51.5 | 43.1 | 46.7 | 46.9 | 48.4 |
|  | C | 50.6 | 49.6 | 50.1 | 54.4 | 50.5 | 47.9 | 47.3 | 49 | 47.2 | 44.9 | 43.5 | 44.2 |
|  | D | 48.2 | 48.4 | 56.3 | 49.2 | 46.4 | 48.5 | 47.1 | 46 | 48.4 | 46.4 | 42.9 | 43.7 |
|  | E | 51.2 | 44.9 | 50.5 | 47.6 | 47.1 | 45.6 | 44.4 | 45.3 | 45.4 | 47.8 | 47.9 | 50.3 |
|  | F | 49.1 | 46.6 | 48.6 | 47.6 | 47.8 | 45.3 | 43.4 | 43.5 | 41.8 | 43.4 | 41.5 | 45.5 |
|  | G | 38.4 | 40.3 | 43.7 | 44.3 | 44.5 | 45.1 | 43.2 | 43.4 | 46 | 45.3 | 44.7 | 42.8 |
|  | H | 17.3 | 24.9 | 35.3 | 41.7 | 36.3 | 31.1 | 38.7 | 38.4 | 39.7 | 39.9 | 41.9 | 35 |

B

|  | 1 | 2 | 3 | 4 | 5 | 6 | 7 | 8 | 9 | 10 | 11 | 12 |
|---|---|---|---|---|---|---|---|---|---|---|---|---|
| A | 0 | 0 | 0 | 0 | 0 | 0 | 0 | 0 | 0 | 0 | 0 | 0 |
| B | 0 | 49.5 | 56.3 | 29.3 | 29.8 | 18.5 | 14.6 | 12.9 | 5.9 | 2.5 | 1.2 | 1 |
| C | 0 | 64 | 64.6 | 63.5 | 58.1 | 47 | 36.1 | 18.2 | 5.1 | 2.3 | 1.7 | 0.8 |
| D | 0 | 65.9 | 64.4 | 62.1 | 56.6 | 46.1 | 32.6 | 16.5 | 5.8 | 2.6 | 1.7 | 0.9 |
| E | 0 | 64 | 67.3 | 67.1 | 60.9 | 47.2 | 38.5 | 19.2 | 6.9 | 2.4 | 3 | 1.5 |
| F | 0 | 63.6 | 62.4 | 58.8 | 48.9 | 42.2 | 31.3 | 18.4 | 5.8 | 1.3 | 1.3 | 1.6 |
| G | 0 | 64.9 | 68.3 | 64.7 | 57.7 | 48.8 | 37.4 | 21.8 | 7.4 | 3.8 | 2.6 | 3.3 |
| H | 0 | 0 | 0 | 0 | 0 | 0 | 0 | 0 | 0 | 0 | 0 | 0 |

To minimize the plate effects observed when forming Aβ fibril directly on the plate, a modified protocol was devised to form Aβ fibrils in a tube overnight, followed by addition to a 96-well plate the next day (protocol 3 in FIG. 7). Protocol 3 eliminated the plate edge effects seen in protocol 2B, as demonstrated by uniformity experiments (Table 2). This protocol also allowed usage of the full 96 wells without any significant changes in the dose response curves (data not shown). Based on the results of these experiments, protocol 3 was selected for further analysis.

Finally, transmission electron microscopy (TEM) was used to confirm that Aβ fibrils and oligomers were formed from protocol 3. Aβ aggregates consisting of a heterogeneous population of fibrils and oligomers were observed using the Aβ preparation from protocol 3 (data not shown). In contrast, Aβ aggregates were not observed when Aβ (1-42) monomers were diluted in aqueous buffer and processed immediately for TEM. Thus, protocol 3 generated Aβ

TABLE 2

Exemplary performance using protocol 3

|  |  | 1 | 2 | 3 | 4 | 5 | 6 | 7 | 8 | 9 | 10 | 11 | 12 |
|---|---|---|---|---|---|---|---|---|---|---|---|---|---|
| 50 µg/mL BART | A | 83.8 | 84.5 | 84.7 | 84.3 | 83.3 | 83.7 | 84.2 | 84.6 | 84.3 | 85.9 | 81.1 | 84.2 |
|  | B | 82.8 | 83.1 | 83.9 | 83.6 | 81.4 | 82.1 | 83.3 | 83 | 82.8 | 81.2 | 84.2 | 83.4 |
|  | C | 81.2 | 81.7 | 82.4 | 84 | 83.4 | 79.7 | 83 | 83.2 | 84.1 | 82.8 | 81.2 | 78.9 |
|  | D | 83 | 81.2 | 81.7 | 82 | 81.3 | 81.3 | 82.2 | 83.4 | 83 | 83.3 | 81.5 | 82.1 |
|  | E | 78.9 | 82.9 | 83.5 | 82.1 | 83,6 | 84 | 84 | 82.3 | 82.3 | 83.4 | 84.5 | 82.9 |
|  | F | 81.8 | 83.4 | 83.5 | 81.4 | 83 | 83.6 | 82.7 | 80 | 82.9 | 82.2 | 82.7 | 83.7 |
|  | G | 83.1 | 80.7 | 84.3 | 82.4 | 83.1 | 83 | 83.5 | 82 | 83.1 | 84 | 81.5 | 80.5 |
|  | H | 82.7 | 84.4 | 82.5 | 83 | 85 | 83.5 | 85.9 | 84.9 | 83.9 | 84.7 | 83.2 | 83 |
| 0.1 µg/mL BART | A | 1.3 | 1.8 | 2.3 | 1.6 | 1.8 | 2.3 | 2.2 | 1.7 | 1.6 | 1.3 | 1.2 | 1 |
|  | B | 0.7 | 1.3 | 1.5 | 2.2 | 1.1 | 1.2 | 1.9 | 1.2 | 1.1 | 2 | 0.8 | 1.1 |
|  | C | 1.7 | 1.3 | 1.1 | 1.4 | 1.3 | 1.1 | 0.6 | 0.7 | 1.5 | 1.2 | 1.3 | 1.5 |
|  | D | 1 | 1.5 | 1 | 1.3 | 0.5 | 1.3 | 1.8 | 0.7 | 0.9 | 0.7 | 1.6 | 0.9 |
|  | E | 1.1 | 1.3 | 0.7 | 1.2 | 1.2 | 0.6 | 0.4 | 1 | 1.2 | 1 | 1.3 | 0.7 |
|  | F | 1 | 1.4 | 0.6 | 0.9 | 1.2 | 0.4 | 0.7 | 1 | 1.1 | 0.8 | 1.1 | 0.7 |
|  | G | 0.9 | 0.5 | 0.6 | 0.5 | 0.5 | 0.5 | 1.2 | 0.8 | 0.7 | 0.7 | 0.7 | 0.6 |
|  | H | 1.1 | 1.1 | 1 | 0.4 | 0.5 | 1.1 | 1.2 | 1.4 | 1.2 | 1.8 | 0.8 | 0.9 | aggregates that resulted in more consistent ADCP assays and contained Aβ fibrils and oligomers as confirmed by electron microscopy.

Example 5

Characterization of the CHO-CD32A H131 Cell Line

Figure 8A:
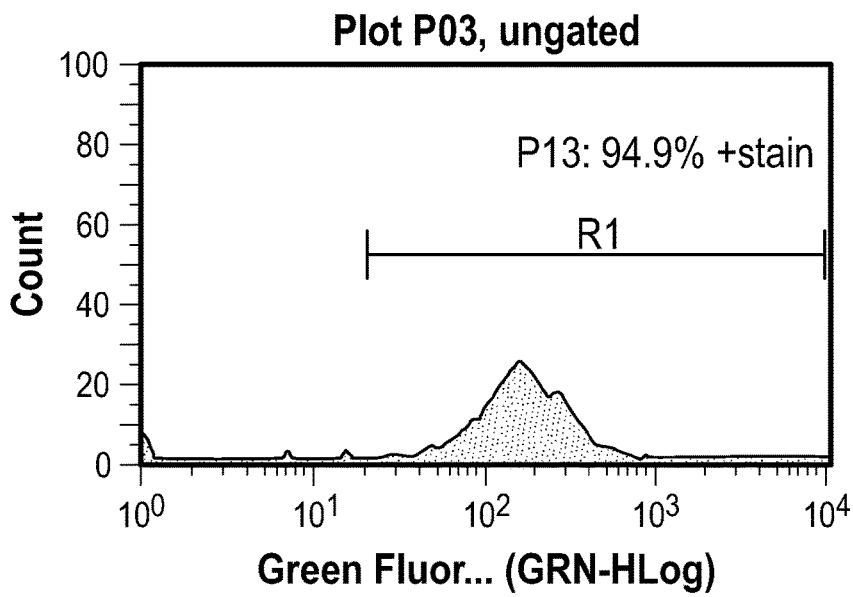
FIG. 8A shows p13 CHO-CD32A H131 cells stained with FITC-labeled anti-CD32A and tested in the ADCP assay.
Figure 8A:
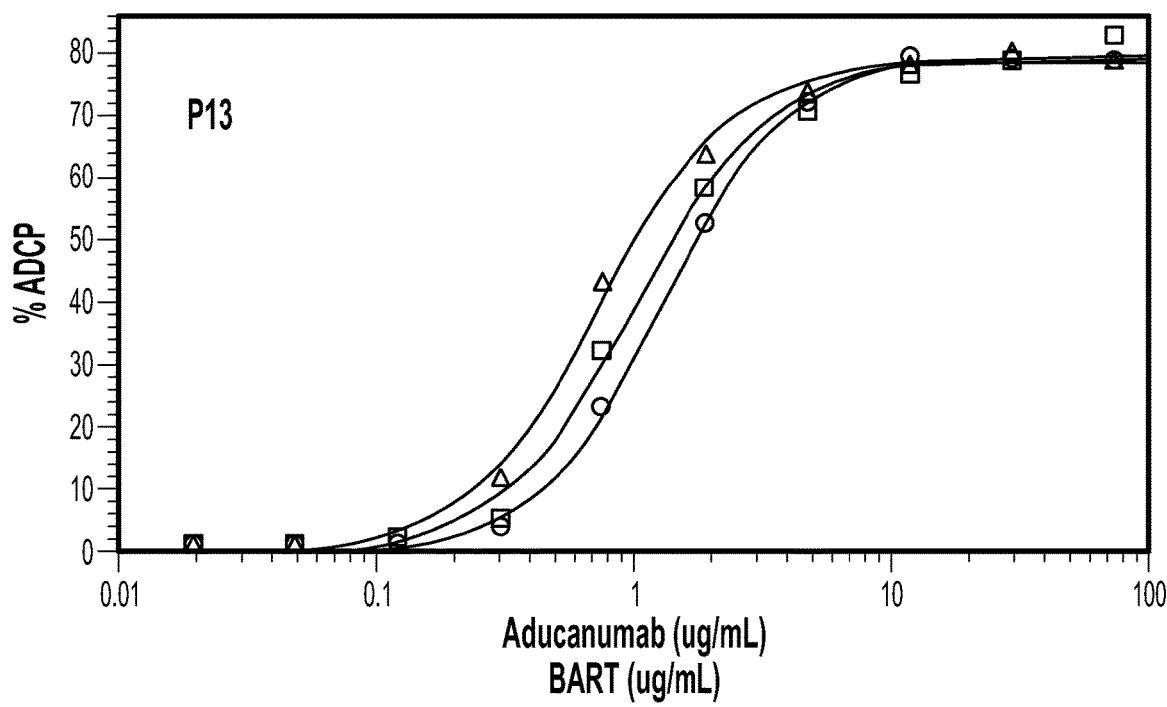
Figure 8B:
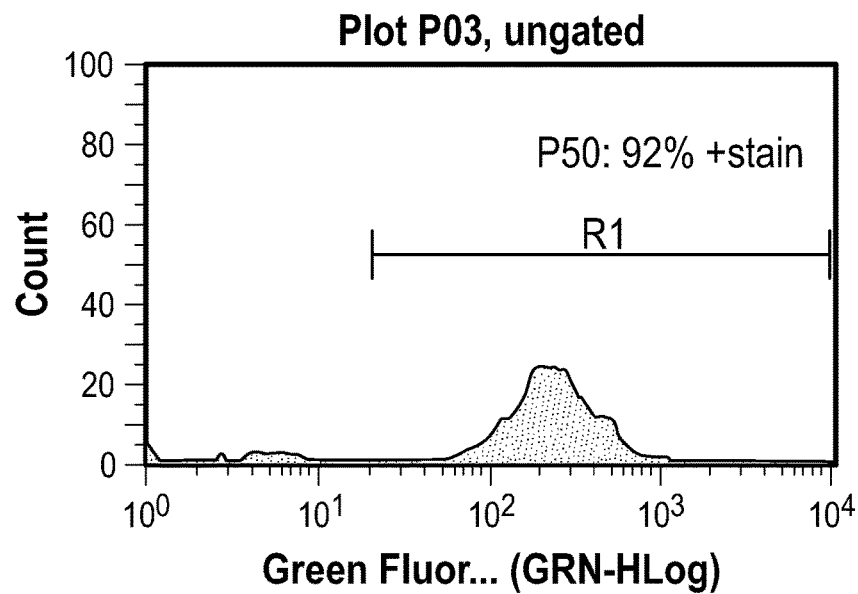
FIG. 8B shows p50 CHO-CD32A H131 cells stained with FITC-labeled anti-CD32A and tested in the ADCP assay.
Figure 8B:
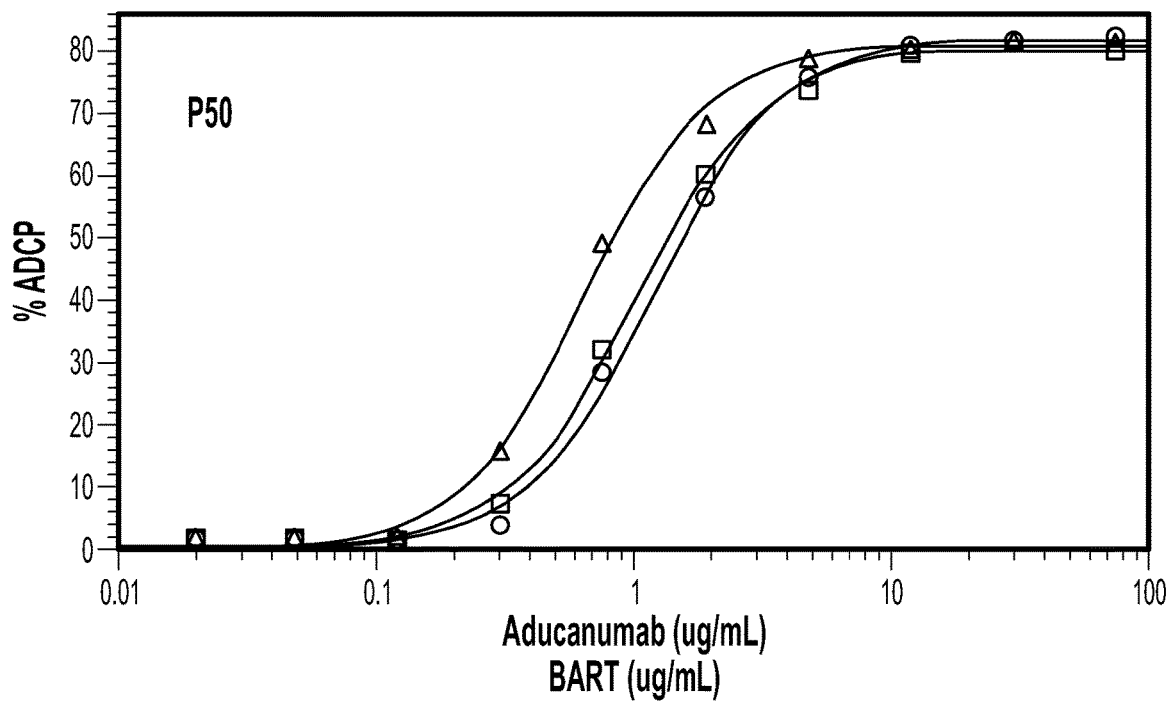

The CHO-CD32A H131 cell line was characterized to determine its robustness in the Aducanumab ADCP assay. Flow cytometry staining of CD32A showed that the expression of CD32A was stable from passage 13 to 50 (FIGS. 8A,B). Passage 50 cells showed similar Aβ uptake activity in terms of signal to noise, slope, relative EC50, and ability to distinguish a mock 150% ADCP activity Aducanumab sample relative to a 100% ADCP activity sample. These data demonstrated that the CHO-CD32A H131 cell line could be used from at least passage 13 to 50.

Figure 9:
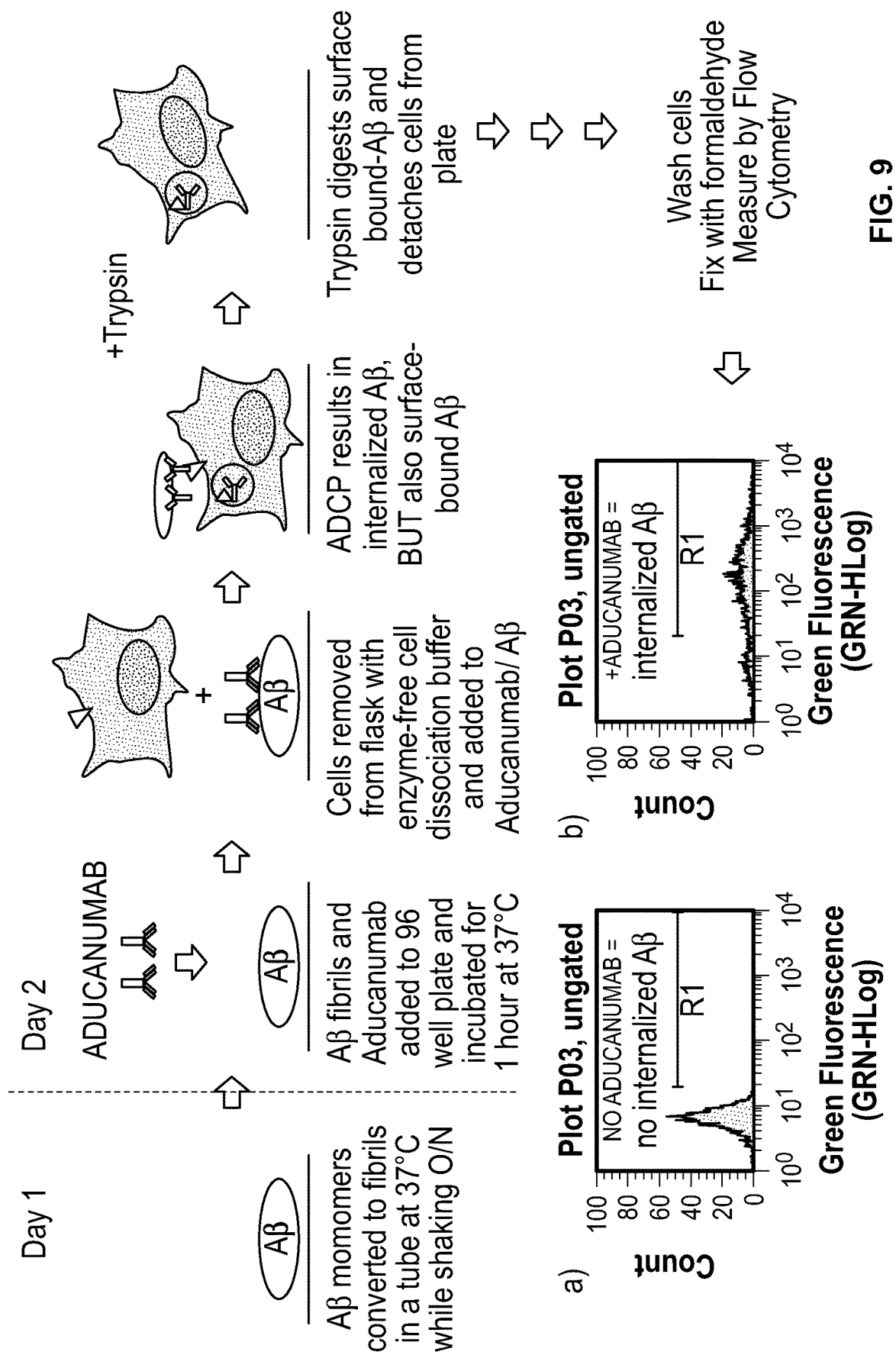
FIG. 9 depicts a schematic of a CHO-CD32A H131 cell line-based assay. DMSO-dissolved HFIP-treatedH488-Aβ (1-42) monomers are converted to Aβ fibrils in a tube at 37° C. while shaking overnight. Aβ fibrils are added to the wells of a round bottom 96 well plate. Dilutions of Aducanumab standard, control, and samples are added to wells containing Aβ fibrils. Aducanumab and Aβ are incubated by shaking at 37° C. for 1 hour. After the incubation, non-enzymatically detached CHO-CD32A H131 cells are added to the plate (60,000 cells/well) and incubated at 37° C. with 5% CO2 for 2 hours. Following ADCP, trypsin is added to the wells to detach adhered cells from the plate surface and digest any cell surface-bound Aβ fibrils. After a series of wash steps, cells are fixed with formaldehyde and the plate is run on a flow cytometer, e.g., a Guava flow cytometer. The % ADCP (% fluorescent positive (+) cells/total cells) is calculated from the cells acquired. The data are processed in Microsoft excel and analyzed with a parallel line analysis (PLA) software package. The relative potency of each sample is calculated.

The CHO-CD32A H131 cell line-based assay format is shown in FIG. 9. DMSO-dissolved HFIP H488-Aβ (1-42) monomers are converted to Aβ fibrils in a tube at 37° C. while shaking overnight. Next, Aβ fibrils are added to the wells of a round bottom 96 well plate. Dilutions of Aducanumab standard, control, and samples are added to wells containing Aβ fibrils. Aducanumab and Aβ are incubated by shaking at 37° C. for 1 hour. After the incubation, non-enzymatically detached CHO-CD32A H131 cells are added to the plate (60,000 cells/well) and incubated at 37° C. with 5% CO2 for 2 hours. Following ADCP, trypsin is added to the wells to detach adhered cells from the plate surface and digest any cell surface-bound Aβ fibrils. After a series of wash steps, cells are fixed with formaldehyde and the plate is run on the Guava flow cytometer. The % ADCP (% fluorescent positive (+) cells/total cells) is calculated from the cells acquired. The data are processed in Microsoft excel and analyzed with a parallel line analysis (PLA) software package. The relative potency of each sample is calculated.

Example 6

Plate Layout and Data Processing

The standards, controls, and samples were placed on a 96-well plate as shown in the layout scheme below (Table 3). Column 12 contained control cells (AP+ cells, no Aducanumab) that were used to adjust settings for the Guava flow cytometer during data acquisition. Plate effects were minimal, and all 96 wells were used.

TABLE 3

Exemplary plate layout

| | 1 | 2 | 3 | 4 | 5 | 6 | 7 | 8 | 9 | 10 | 11 | 12 |
|---|---|---|---|---|---|---|---|---|---|---|---|---|
| A | | | | | Standard | | | | | | | Control Cells |
| B | | | | | Sample | | | | | | | (abeta + cells; |
| C | | | | | Control | | | | | | | NO BART |
| D | | | | | Sample | | | | | | | |
| E | | | | | Standard | | | | | | | |
| F | | | | | Sample | | | | | | | |
| G | | | | | Standard | | | | | | | |
| H | | | | | Control | | | | | | | |

For data processing, only one assay plate was run for each sample being tested. The data from the assay plate was averaged using the scheme below (Table 4). The standard and sample were run in triplicate, and the control was run in duplicate. Replicates were averaged before importing the data into the PLA software in the schematic shown. The independent replicates of "Standard" (STD), "Control" (CTL) and "Sample" (SAMP) on this "average plate" were imported into PLA with an A1L8 module for analysis. After importing data into PLA, a report is generated and provides data values, test of validity data, and potency estimations (Table 5).

TABLE 4

Exemplary plate averaging scheme

| Assay Plate | | Average Plate |
|---|---|---|
| Standard | → | Standard |
| Sample | | Control |
| Control | | Sample |
| Sample | | |
| Standard | | |
| Sample | | |
| Standard | | |
| Control | | |

TABLE 5

Exemplary PLA report

Unknown: CNTL

| Dose Values | 50.0 | 25.0 | 12.5 | 6.25 | 3.125 | 1.563 | 0.781 |
|---|---|---|---|---|---|---|---|
| Response 1 | 85.0 | 84.95 | 86.4 | 87.1 | 79.7 | 67.05 | 32.5 |
| Dose Values | 0.391 | 0.195 | 0.098 | 0.049 | | | |
| Response 1 | 11.5 | 2.8 | 1.25 | 1.2 | | | |

Standard: STD

| Dose Values | 50.0 | 25.0 | 12.5 | 6.25 | 3.125 | 1.563 | 0.781 |
|---|---|---|---|---|---|---|---|
| Response 1 | 84.866667 | 86.2 | 86.533333 | 87.066667 | 81.066667 | 65.266667 | 36.233333 |
| Does Values | 0.391 | 0.195 | 0.098 | 0.049 | | | |
| Response 1 | 7.2 | 2.766667 | 1.1 | 1.233333 | | | |

Test of Validity

| Test of Regression [F = 4298.260 > Fcritical = 3.344] | Test Passed! |
|---|---|
| Test of Linearity [F = 0.000 < Fcritical = 0.000] | Test Passed! |
| Test of Parallelism [F = 0.180 < Fcritical = 3.344] | Test Passed! |

TABLE 5-continued

Exemplary PLA report

Potency Estimation

|  | CNTL vs. STD |
|---|---|
| Potency Ratio incl. Pre-Dilution Factors | 0.989 |
| 95.0% Confidence Limits | 0.926-1.056 |
| Relative Confidence Limits | 93.6%-106.8% (13.2%) |

Example 7

Assay Qualification

Figure 10:
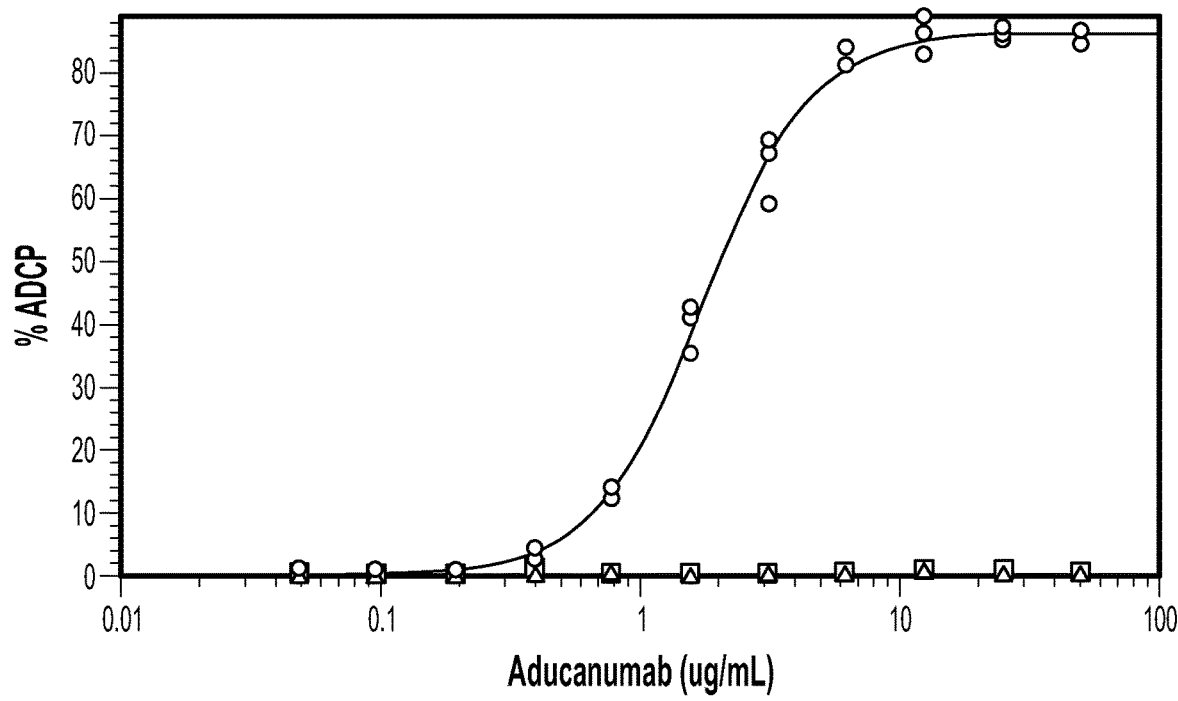
FIG. 10 shows results from an antibody specificity test. Three antibodies, Aducanumab and two negative control antibodies, were tested in the ADCP assay. % ADCP was measured, and the results were graphed with SoftMax Pro.

Assay specificity was tested using two negative control antibodies. Neither negative control antibody tested mediated ADCP of Aβ fibrils by CHO-CD32A cells, demonstrating that the dose-dependent ADCP of Aβ fibrils required both binding to Aβ and CD32A binding (FIG. 10).

Assay qualification studies were performed using Aducanumab samples created with 50%, 75%, 100%, 125%, and 150% of the concentration of reference standard diluted in assay medium. The samples were tested multiple times and in different time periods. Table 6 summarizes testing results of the qualification samples. Each measured potency value for the samples resulted from the average of three dose response curves on a single plate. As observed by the numbers listed in the column of "Mean RP %" (measured potency of sample), the mean potency of each sample was close to the expected potency. The average recovery is 102.1%. The assay precision was calculated to be 10.2%.

TABLE 6

Accuracy and precision of the ADCP assay

| Expected Potency | Assay # | Control RP % | Sample RP % | Mean RP % | Recovery | Mean Recovery |
|---|---|---|---|---|---|---|
| 49% | Assay 1 | 114.8% | 48.6% | 50% | 99.2% | 101.4% |
| | Assay 2 | 112.7% | 53.1% | | 108.4% | |
| | Assay 3 | 102.9% | 44.8% | | 91.4% | |
| | Assay 4 | 107.5% | 53.4% | | 106.6% | |
| 73% | Assay 5 | 98.6% | 71.5% | 72.9% | 97.9% | 99.8% |
| | Assay 6 | 101.1% | 71.2% | | 97.5% | |
| | Assay 7 | 103.8% | 75.9% | | 104.0% | |
| 95% | Assay 8 | 98.9% | 87.1% | 90.5% | 87.1% | 90.5% |
| | Assay 9 | 93.8% | 89.7% | | 89.7% | |
| | Assay 10 | 109.1% | 94.6% | | 94.6% | |
| 130% | Assay 11 | 87.8% | 132.6% | 134.5% | 102.0% | 103.5% |
| | Assay 12 | 91.6% | 121.5% | | 93.5% | |
| | Assay 13 | 112.3% | 149.5% | | 115.0% | |
| 149% | Assay 14 | 107.5% | 152.4% | 166.2% | 102.3% | 112.0% |
| | Assay 15 | 87.7% | 154.5% | | 103.7% | |
| | Assay 16 | 97.9% | 168.4% | | 113.0% | |
| | Assay 17 | 122.6% | 189.5% | | 129.0% | |

| | Control | Sample |
|---|---|---|
| Accuracy | 103% | 102.1% |
| Precision | 9.5% | 10.2% |

Based on the results from qualification studies, the assay linearity was confirmed by plotting measured mean relative potency versus expected relative potency (data not shown). The assay was linear in the tested range of 50-150%, as indicated by a regression line slope of 1.1458 and a correlation coefficient ($R^2$) of 0.9852.

Figure 11:
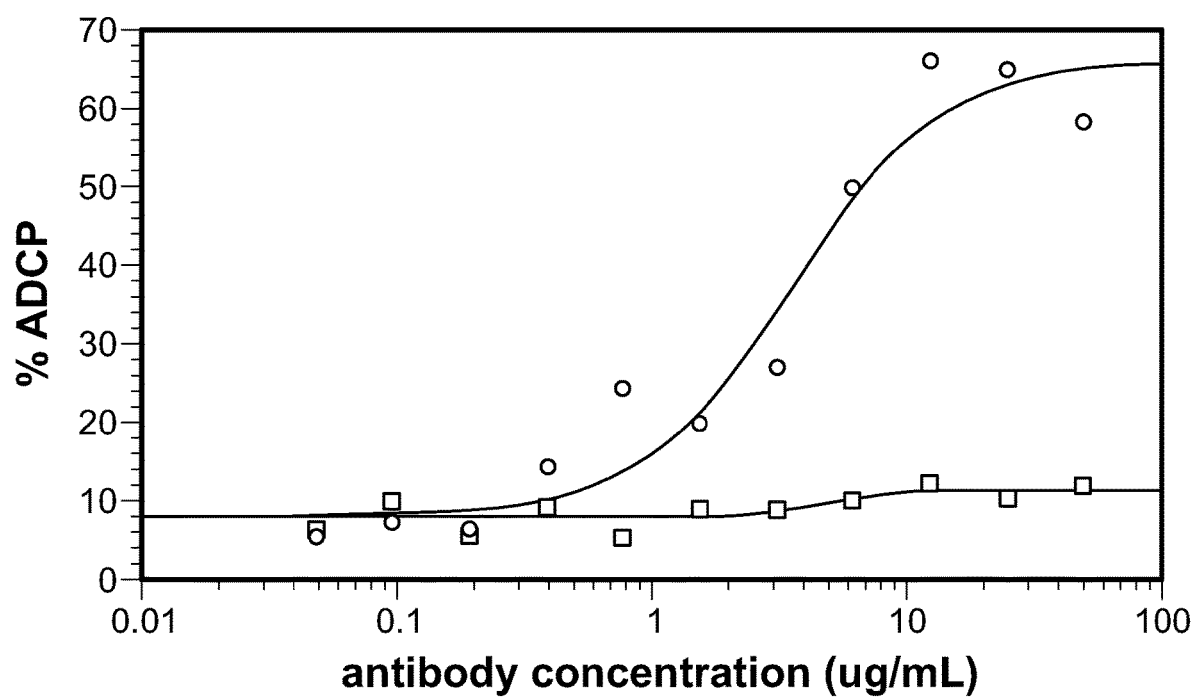
FIG. 11 is a graph of % ADCP using an Aβ aggregate-specific antibody (circles) and an Aβ monomer-specific control antibody (squares).

The dose-dependent ADCP of Aβ fibrils is specific (FIG. 11) and requires actin-mediated internalization, CD32 expression, and Fc effector function. The ADCP assay has high accuracy and precision and may be used for product characterization, and/or stability tests.

The invention claimed is:

1. A method of measuring antibody-dependent cell-mediated phagocytosis (ADCP) of an aggregated protein comprising the steps of:
    a) monomerizing and fluorescently labeling the aggregated protein,
    b) incubating the monomerized and fluorescently labeled protein for a time period sufficient to form fluorescently labeled aggregated protein,
    c) contacting the fluorescently labeled aggregated protein with a protein-specific antibody for a time period sufficient to permit the formation of an antibody-protein complex,
    d) contacting the antibody-protein complex with a population of phagocytic cells for a time period sufficient to permit phagocytosis of the antibody-protein complex, wherein the phagocytic cells may be adherent cells, and the adherent phagocytic cells are removed from a surface using non-enzymatic cell dissociation buffer prior to said step of contacting the antibody-protein complex with the population of phagocytic cells,
    e) removing surface-bound protein from the surface of the phagocytic cells, and
    f) determining phagocytosis of the antibody-protein complex by measuring intracellular fluorescence in the phagocytic cells using flow cytometry, wherein the intracellular fluorescence is measured using 5,000 or fewer events.

2. The method of claim 1, wherein the protein is monomerized using hydroxyfluoro-isopropanol.

3. The method of claim 1, wherein the protein monomerization is maintained using lyophilization.

4. The method of claim 1, wherein the monomerized protein is reconstituted in Dimethyl Sulfoxide (DMSO) to reduce seed formation.

5. The method of claim 1, wherein the surface-bound proteins are removed by enzymatic digestion.

6. The method of claim 5, wherein the surface-bound proteins are removed by trypsin.

7. The method of claim 1, wherein the phagocytic cell is fixed following phagocytosis using formaldehyde, paraformaldehyde, or glutaraldehyde.

8. The method of claim 1, wherein the antibody is selected from the group consisting of an anti-β amyloid antibody, an anti-tau antibody, an anti-synuclein antibody, an anti-TAR DNA-binding 43 (TDP-43) antibody, an anti-neuroserpin antibody, an anti-Fused in Sarcoma (FUS) antibody, an anti-PrP$^{Sc}$ antibody, an anti-Superoxide Dismutase (SOD1) antibody, an anti-ubiquilin antibody, an anti-optineurin antibody, an anti-British Amyloid (ABri) antibody, and an anti-Danish Amyloid (ADan) antibody.

9. The method of claim 8, wherein the antibody is an anti-β amyloid antibody that is selected from the group consisting of Aducanumab, Bapineuzumab, Crenezumab, Gantenerumab, BAN2401, Ponezumab, and Solanezumab.

10. The method of claim 1, wherein the protein-specific antibody binds strongly to protein aggregates and weakly to protein monomers.

11. The method of claim 1, wherein the protein is Aβ and the antibody is an Aβ-specific antibody.

12. The method of claim 11, wherein the Aβ-specific antibody binds strongly to AP aggregates and weakly to Aβ monomers.

13. The method of claim 1, wherein the phagocytic cell is a cell that is naturally capable of phagocytosis.

14. The method of claim 13, wherein the Fc receptor is a FcγR, FcαR, or FcεR receptor.

15. The method of claim 14, wherein the Fc receptor is a FcγR2a/CD32A receptor.

16. The method of claim 1, wherein the phagocytic cell is a cell that is not naturally capable of phagocytosis and further engineered to comprise a heterologous sequence encoding a Fc receptor.

17. The method of claim 16, wherein the Fc receptor is a human Fc receptor.

18. The method of claim 1, wherein the phagocytic cell is selected from the group consisting of BV-2, THP-1, CHO, 293-T, 3T3, 4T1, 721, 9L, A2780, A172, A20, A253, A431, A-549, ALC, B16, B35, BCP-1, BEAS-2B, bEnd.3, BHK-21, BR293, BxPC3, C3H-10T1/2, C6, Cal-27, COR-L23, COS-7, CIVIL T1, CMT, CT26, D17, DH82, DU145, DuCaP, EL4, EM2, EM3, EMT6/AR1, FM3, H1299, H69, HB54, HB55, HCA2, HEK-293, HeLa, Hepa1c1c7, HL-60, HMEC, HT-29, HUVEC, Jurkat, J558L, JY, K562, Ku812, KCL22, KG1, KY01, MCF-7, RBL, Saos-2, SKBR3, SKOV-3, T2, T-47D, T84, U373, U937, Vero, and J774.

19. The method of claim 1, wherein the phagocytic cell is a CHO-CD32A cell.

20. The method of claim 19, wherein the CHO-CD32A cell is a CHO-CD32A H131 cell.

21. The method of claim 1, wherein a flow cytometer is used to measure the intracellular fluorescence.

22. The method of claim 21, wherein fluorescence-activated cell sorting flow cytometer.

23. The method of claim 21, wherein the flow cytometer is a sheath-flow cytometer.

24. The method of claim 21, wherein the flow cytometer is a flow-cell cytometer.

25. The method of claim 21, wherein the intracellular fluorescence measurements are determined using about 500, 1000, 1500, 2000, 2500, 3000, 3500, 4000, or 5000 events.

26. The method of claim 21, wherein intracellular fluorescence is measured as a number of fluorescence-positive cells over a total number of cells.

27. The method of claim 21, wherein the intracellular fluorescence measurements are determined using 500 to 5,000 events.

28. The method of claim 1, wherein the phagocytic cell is not BV-2.

29. A method of measuring antibody-dependent cell-mediated phagocytosis (ADCP) of an aggregated beta amyloid protein comprising the steps of:
  a) monomerizing and fluorescently labeling the aggregated beta amyloid protein,
  b) incubating the monomerized and fluorescently labeled beta amyloid protein for a time period sufficient to form fluorescently labeled aggregated beta amyloid protein,
  c) contacting the fluorescently labeled aggregated beta amyloid protein with an anti-beta amyloid-specific antibody for a time period sufficient to permit the formation of an antibody-protein complex,
  d) contacting the antibody-protein complex with a population of CHO-CD32A cells for a time period sufficient to permit phagocytosis of the antibody-protein complex, wherein adherent CHO-CD32A cells are removed from a surface using non-enzymatic cell dissociation buffer prior to said step of contacting the antibody-protein complex with the population of CHO-CD32A cells,
  e) removing surface-bound protein from the surface of the CHO-CD32A cells, and
  f) determining phagocytosis of the antibody-protein complex by measuring intracellular fluorescence in the CHO-CD32A cells using flow cytometry, wherein the intracellular fluorescence is measured using 5,000 or fewer events.

30. The method of claim 29, wherein the beta amyloid protein is monomerized using hydroxyfluoro-isopropanol.

31. The method of claim 29, wherein the beta amyloid protein monomerization is maintained using lyophilization.

32. The method of claim 29, wherein the monomerized beta amyloid protein is reconstituted in DMSO to reduce seed formation.

33. The method of claim 29, wherein the surface-bound proteins are removed by enzymatic digestion.

34. The method of claim 33, wherein the surface-bound proteins are removed by trypsin.

35. The method of claim 29, wherein the CHO-CD32A cells are fixed following phagocytosis using formaldehyde, paraformaldehyde, or glutaraldehyde.

36. The method of claim 29, wherein the anti-beta amyloid antibody is selected from the group consisting of Aducanumab, Bapineuzumab, Crenezumab, Gantenerumab, BAN2401, Ponezumab, and Solanezumab.

37. The method of claim 29, wherein the anti-beta amyloid antibody is Aducanumab.

38. The method of claim 29, wherein the anti-beta amyloid antibody is BAN2401.

39. The method of claim 29, wherein the CHO-CD32A cell is a CHO-CD32A H131 cell.

40. The method of claim 29, wherein a flow cytometer is used to measure the intracellular fluorescence.

41. The method of claim 40, wherein the flow cytometer is a fluorescence-activated cell sorting flow cytometer.

42. The method of claim 40, wherein the flow cytometer is a sheath-flow cytometer.

43. The method of claim 40, wherein the flow cytometer is a flow-cell cytometer.

44. The method of claim 40, wherein the intracellular fluorescence measurements are determined using 500 to 5,000 events.

45. The method of claim 40, wherein intracellular fluorescence is measured as a number of fluorescence-positive cells over a total number of cells.

46. The method of claim 29, wherein the monomerizing is performed after the aggregated beta amyloid protein is labeled.

47. The method of claim 29, wherein the monomerizing is performed at substantially the same time as the aggregated beta amyloid protein is labeled.

* * * * *